United States Patent
Loewen et al.

(10) Patent No.: US 10,940,141 B1
(45) Date of Patent: Mar. 9, 2021

(54) METHODS FOR THE ADMINISTRATION OF CERTAIN VMAT2 INHIBITORS

(71) Applicant: Neurocrine Biosciences, Inc., San Diego, CA (US)

(72) Inventors: Gordon Raphael Loewen, Solana Beach, CA (US); Sha Rosa Luo, San Diego, CA (US)

(73) Assignee: Neurocrine Biosciences, Inc., San Diego, CA (US)

(*) Notice: Subject to any disclaimer, the term of this patent is extended or adjusted under 35 U.S.C. 154(b) by 0 days.

(21) Appl. No.: 16/989,206

(22) Filed: Aug. 10, 2020

Related U.S. Application Data

(60) Provisional application No. 62/890,697, filed on Aug. 23, 2019, provisional application No. 63/028,754, filed on May 22, 2020.

(51) Int. Cl.
  *A61K 31/4375* (2006.01)
  *A61P 13/12* (2006.01)

(52) U.S. Cl.
  CPC .......... *A61K 31/4375* (2013.01); *A61P 13/12* (2018.01)

(58) Field of Classification Search
  CPC .......................... A61K 31/4375; A61P 13/12
  See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,328,245 A | 5/1982 | Yu et al. | |
| 4,409,239 A | 10/1983 | Yu | |
| 4,410,545 A | 10/1983 | Yu et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,612,059 A | 3/1997 | Cardinal et al. | |
| 5,639,476 A | 6/1997 | Oshlack et al. | |
| 5,639,480 A | 6/1997 | Bodmer et al. | |
| 5,674,533 A | 10/1997 | Santus et al. | |
| 5,698,220 A | 12/1997 | Cardinal et al. | |
| 5,709,874 A | 1/1998 | Hanson et al. | |
| 5,733,566 A | 3/1998 | Lewis | |
| 5,739,108 A | 4/1998 | Mitchell | |
| 5,759,542 A | 6/1998 | Gorewich | |

(Continued)

FOREIGN PATENT DOCUMENTS

| EP | 1716145 | 11/2006 |
|---|---|---|
| JP | 57-077697 | 5/1982 |

(Continued)

OTHER PUBLICATIONS

U.S. Appl. No. 16/481,037, O'Brien et al., filed Jul. 25, 2019.

(Continued)

*Primary Examiner* — San Ming R Hui
(74) *Attorney, Agent, or Firm* — Fish & Richardson P.C.

(57) ABSTRACT

Provided is a method of administering a vesicular monoamine transporter 2 (VMAT2) inhibitor to a subject in need thereof, wherein the subject has severe renal impairment.

30 Claims, 1 Drawing Sheet

(56) References Cited

U.S. PATENT DOCUMENTS

| | | | |
|---|---|---|---|
| 5,798,119 | A | 8/1998 | Heibig et al. |
| 5,840,674 | A | 11/1998 | Yatvin et al. |
| 5,891,474 | A | 4/1999 | Busetti et al. |
| 5,900,252 | A | 5/1999 | Calanchi et al. |
| 5,922,356 | A | 7/1999 | Koseki et al. |
| 5,972,366 | A | 10/1999 | Heynes et al. |
| 5,972,891 | A | 10/1999 | Kamei et al. |
| 5,980,945 | A | 11/1999 | Ruiz |
| 5,985,307 | A | 11/1999 | Hanson et al. |
| 5,993,855 | A | 11/1999 | Yoshimoto et al. |
| 6,004,534 | A | 12/1999 | Langer et al. |
| 6,039,975 | A | 3/2000 | Shah et al. |
| 6,045,830 | A | 4/2000 | Igari et al. |
| 6,048,736 | A | 4/2000 | Kosak |
| 6,060,082 | A | 5/2000 | Chen et al. |
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,197,350 | B1 | 3/2001 | Yamagata et al. |
| 6,248,363 | B1 | 6/2001 | Patel et al. |
| 6,253,872 | B1 | 7/2001 | Neumann |
| 6,264,970 | B1 | 7/2001 | Hata et al. |
| 6,267,981 | B1 | 7/2001 | Okamoto et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,350,458 | B1 | 2/2002 | Modi |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 8,039,627 | B2 | 10/2011 | Gano et al. |
| 8,357,697 | B2 | 1/2013 | Gano et al. |
| 8,524,733 | B2 | 9/2013 | Gant et al. |
| 9,714,246 | B2 | 7/2017 | Ashweek et al. |
| 9,782,398 | B2 | 10/2017 | Hoare et al. |
| 10,065,952 | B2 | 9/2018 | McGee et al. |
| 10,160,757 | B2 | 12/2018 | McGee et al. |
| 10,689,380 | B1 | 6/2020 | Lopez |
| 2006/0051345 | A1 | 3/2006 | Frohna |
| 2006/0241082 | A1 | 10/2006 | Fleckenstein et al. |
| 2008/0108645 | A1 | 5/2008 | Tridgett et al. |
| 2008/0167337 | A1 | 7/2008 | Gano |
| 2009/0209755 | A1 | 8/2009 | Suzuki et al. |
| 2010/0076087 | A1 | 3/2010 | Gant et al. |
| 2011/0053866 | A1 | 3/2011 | Duffield et al. |
| 2012/0003330 | A1 | 1/2012 | Gant et al. |
| 2012/0077839 | A1 | 3/2012 | Gano |
| 2014/0187505 | A1 | 7/2014 | Pollard |
| 2014/0341994 | A1 | 11/2014 | Sommer et al. |
| 2015/0004231 | A1 | 1/2015 | Sommer et al. |
| 2015/0025086 | A1 | 1/2015 | Dressman et al. |
| 2016/0030414 | A1 | 2/2016 | Gant et al. |
| 2016/0339011 | A1 | 11/2016 | Hoare et al. |
| 2016/0346200 | A1 | 12/2016 | Sommer et al. |
| 2016/0346270 | A1 | 12/2016 | Stamler |
| 2017/0071932 | A1 | 3/2017 | O'Brien |
| 2017/0145008 | A1 | 5/2017 | McGee et al. |
| 2017/0183346 | A1 | 6/2017 | McGee et al. |
| 2018/0085364 | A1 | 3/2018 | Hoare |
| 2018/0280374 | A1 | 10/2018 | Duffield et al. |
| 2018/0333409 | A1 | 11/2018 | Srinivasan et al. |
| 2019/0015396 | A1 | 1/2019 | O'Brien et al. |
| 2019/0262328 | A1 | 8/2019 | Srinivasan et al. |
| 2019/0381016 | A1 | 12/2019 | O'Brien et al. |
| 2019/0381029 | A1 | 12/2019 | Hoare et al. |
| 2020/0078352 | A1 | 3/2020 | O'Brien et al. |
| 2020/0093808 | A1 | 3/2020 | O'Brien et al. |
| 2020/0101063 | A1 | 4/2020 | O'Brien et al. |
| 2020/0179352 | A1 | 6/2020 | O'Brien |
| 2020/0181140 | A1 | 6/2020 | McGee et al. |
| 2020/0206215 | A1 | 7/2020 | Hoare et al. |
| 2020/0230127 | A1 | 7/2020 | O'Brien et al. |
| 2020/0268724 | A1 | 8/2020 | O'Brien et al. |
| 2020/0268725 | A1 | 8/2020 | O'Brien et al. |
| 2020/0268743 | A1 | 8/2020 | O'Brien et al. |
| 2020/0268744 | A1 | 8/2020 | O'Brien et al. |
| 2020/0268745 | A1 | 8/2020 | O'Brien et al. |
| 2020/0276184 | A1 | 9/2020 | Moore, Jr. et al. |
| 2020/0338066 | A1 | 10/2020 | O'Brien et al. |
| 2020/0339574 | A1 | 10/2020 | McGee et al. |
| 2020/0339575 | A1 | 10/2020 | McGee et al. |
| 2020/0339576 | A1 | 10/2020 | McGee et al. |
| 2020/0347054 | A1 | 11/2020 | McGee et al. |
| 2020/0347055 | A1 | 11/2020 | McGee et al. |
| 2020/0347056 | A1 | 11/2020 | McGee et al. |
| 2020/0347057 | A1 | 11/2020 | McGee et al. |
| 2020/0360354 | A1 | 11/2020 | Liang et al. |

FOREIGN PATENT DOCUMENTS

| | | | |
|---|---|---|---|
| JP | 57-209225 | | 12/1982 |
| WO | WO 1991/019498 | | 12/1991 |
| WO | WO 1998/011897 | | 3/1998 |
| WO | WO 2000/024399 | | 5/2000 |
| WO | WO 2002/017918 | | 3/2002 |
| WO | WO 2005/077946 | | 8/2005 |
| WO | WO 2007/017654 | | 2/2007 |
| WO | WO 2008/058261 | | 5/2008 |
| WO | WO 2009/056885 | | 5/2009 |
| WO | WO 2010/018408 | | 2/2010 |
| WO | WO 2010/026435 | | 3/2010 |
| WO | WO 2010/026436 | | 3/2010 |
| WO | WO 2010/044961 | | 4/2010 |
| WO | WO 2010/044981 | | 4/2010 |
| WO | WO 2011/019956 | | 2/2011 |
| WO | WO 2011/153157 | | 12/2011 |
| WO | WO 2014/047167 | | 3/2014 |
| WO | WO 2014/120654 | | 8/2014 |
| WO | WO 2015/077521 | | 5/2015 |
| WO | WO 2015/112707 | | 7/2015 |
| WO | WO 2015/120110 | | 8/2015 |
| WO | WO 2015/120317 | | 8/2015 |
| WO | WO 2015/171802 | | 11/2015 |
| WO | WO-2015171802 A1 * | 11/2015 | ............. A61P 43/00 |
| WO | WO 2016/127133 | | 8/2016 |
| WO | WO 2016/144901 | | 9/2016 |
| WO | WO 2016/210180 | | 12/2016 |
| WO | WO 2017/075340 | | 5/2017 |
| WO | WO 2017/112857 | | 6/2017 |
| WO | WO 2018/102673 | | 6/2018 |
| WO | WO 2018/140092 | | 8/2018 |
| WO | WO 2018/140093 | | 8/2018 |
| WO | WO 2018/140094 | | 8/2018 |
| WO | WO 2018/140095 | | 8/2018 |
| WO | WO 2018/140096 | | 8/2018 |
| WO | WO 2018/200605 | | 11/2018 |
| WO | WO 2019/060322 | | 3/2019 |
| WO | WO 2019/074492 | | 4/2019 |
| WO | WO 2019/241555 | | 12/2019 |
| WO | WO 2020/037022 | | 2/2020 |

OTHER PUBLICATIONS

U.S. Appl. No. 16/701,339, O'Brien et al., filed Dec. 3, 2019.
U.S. Appl. No. 16/983,334, Liang et al., filed Aug. 3, 2020.
U.S. Appl. No. 16/989,206, Loewen et al., filed Aug. 10, 2020.
U.S. Appl. No. 17/005,425, O'Brien, filed Aug. 28, 2020.
U.S. Appl. No. 17/021,362, O'Brien et al., filed Sep. 15, 2020.
Cummings et al., "Deuterium tetrabenazine for tardive dyskinesia," Clinical Schizophrenia & Related Psychoses, 2018, 214-220.
Preswick Pharmaceuticals et al., "Xenazine (tetrabenazine) tablets," 2008, retrieved from URL: https://accessdata.fda.gov/drugsatfda_docs/label/2011/021894s0051b1.pdj, retrieved on Jul. 28, 2020, 1 page.
Davis et al., "Center for Drug Evaluation and Research," Medical Reviews(s), Jun. 1, 2017, Accessed on Sep. 30, 2020, retrieved from URL<https://www.accessdata.fda.gov/drugsatfda_docs/nda/2017/209241Orig1s000MedR.pdf>, 297 pages.

(56) References Cited

OTHER PUBLICATIONS

Fda.gov [online], U.S. Food & Drug Administration Drug Approvals and Databases, "Ingrezza (valbenazine) Capsules," dated Jun. 1, 2017, retrieved on Sep. 30, 2020, retrieved from URL<https://www.accessdata.fda.gov/drugsatfda_docs/nda/2017/209241Orig1s000TOC.cfm>, 2 pages.
Siegert et al., "Efficacy and Safety of Valbenazine (NBI-98854) in Subjects with Tardive Dyskinesia: Results of a Long-Term Study (KINECT 3 Extension)," Poster Presented at the Xxii World Congress on Parkinson's Disease and Related Disorders, Nov. 12-15, 2017, 1 page.
Singer et al., "Assessing the Effectiveness of Valbenazine in the Treatment of Tardive Dyskinesia as Determined by the AIMS and PGIC: Results from the KINECT 4 Trial," Poster Presented at the 22nd Annual International Congress of Parkinson's Disease and Movement Disorders, Oct. 5-9, 2018, 1 page.
U.S. Appl. No. 16/481,033, O'Brien et al., filed Jul. 25, 2019.
U.S. Appl. No. 16/481,034, O'Brien et al., filed Jul. 25, 2019.
U.S. Appl. No. 16/509,552, McGee et al., filed Jul. 12, 2019.
U.S. Appl. No. 16/608,521, O'Brien, filed Oct. 25, 2019.
U.S. Appl. No. 16/646,866, Moore Jr. et al., filed Mar. 12, 2020.
U.S. Appl. No. 16/651,887, O'Brien et al., filed Mar. 27, 2020.
U.S. Appl. No. 16/662,346, McGee et al., filed Oct. 24, 2019.
U.S. Appl. No. 16/754,658, O'Brien et al., filed Apr. 8, 2020.
U.S. Appl. No. 16/817,723, Hoare et al., filed Mar. 13, 2020.
U.S. Appl. No. 16/845,134, O'Brien et al., filed Apr. 10, 2020.
U.S. Appl. No. 16/870,423, O'Brien et al., filed May 8, 2020.
U.S. Appl. No. 16/870,572, O'Brien et al., filed May 8, 2020.
U.S. Appl. No. 16/870,706, O'Brien et al., filed May 8, 2020.
U.S. Appl. No. 16/870,823, O'Brien et al., filed May 8, 2020.
U.S. Appl. No. 16/871,528, O'Brien et al., filed May 11, 2020.
U.S. Appl. No. 16/899,641, McGee et al., filed Jun. 12, 2020.
U.S. Appl. No. 16/899,645, McGee et al., filed Jun. 12, 2020.
U.S. Appl. No. 16/899,654, McGee et al., filed Jun. 12, 2020.
U.S. Appl. No. 16/929,694, McGee et al., filed Jul. 15, 2020.
U.S. Appl. No. 16/929,696, McGee et al., filed Jul. 15, 2020.
U.S. Appl. No. 16/929,714, McGee et al., filed Jul. 15, 2020.
U.S. Appl. No. 16/929,716, McGee et al., filed Jul. 15, 2020.
"Cytochrome P450 Oxidoreductase (POR) Deficiency," GeneDx, 2016, 5 pages.
"Neurocrine Valbenazine," Science IP Order 3198386, Oct. 2, 2019, 92 pages.
[No Author Listed], "Cytochrome P450 3A4 and 3A5 known drug interaction chart," 2014, 2 pages.
[No Author Listed], "Drug interactions with CYP3A inducers and inhibitors for Torisel (temsirolimus) injection," Wyeth Pharmaceuticals, 2008, 12 pages.
[No Author Listed], "Physician guidelines: drugs metabolized by cytochrome P450's," Genelex Corporation, 2005, 4 pages.
[No Author Listed],"Ingrezza Prescription Information," Neurocrine Biosciences, Apr. 2017, 16 pages.
Alexander et al., "Increased aggression in males in transgenic Tg2576 mouse model of Alzheimer's disease," Behav Brain Res., 216(1):77-83.
Anonymous, "11th Annual Meeting Schedule," ASENT, Mar. 5-7, 2009, 3 pages.
Anonymous, "12th Annual Meeting Program," ASENT, Bethesda, Maryland, Mar. 4-6, 2010, 1 page.
Anonymous, "Neurocrine Announces Phase IIb Results of VMAT2 Inhibitor NBI-98854 for Treatment of Tardive Dyskinesia," Neurocrine Biosciences: Investors: PressRelease, Sep. 9, 2013, [retrieved on Dec. 13, 2018] retrieved from URL<http://phoenix.corporate-ir.net/phoenix.zhtml?c=68817&p=irol-newsArticle_Print&ID=1853185>, 7 pages.
Australian Office Action in AU Appln. No. 2015256012, dated May 26, 2020, 5 pages.
Ballard et al., "Management of Agitation and Aggression Associated with Alzheimer's disease: controversies and possible solutions," Curr Opin in Psych., Nov. 2009, 22(6):532-540.

Ballard et al., "Neuroleptic drugs in dementia: benefits and harm," Nat Rev Neurosci., Jun. 2006, 7:492-500.
Ballard et al., "Quetiapine and rivastigmine and cognitive decline in Alzheimer's disease: randomised double blind placebo controlled trial," BMJ, Apr. 16, 2005, 330:874-877.
Bastin et al., "Salt Selection and Optimisation Procedures for Pharmaceutical New Chemical Entities," Organic Process Res. Dev., 2000, 4(5):427-435.
Bauer, "Pharmaceutical Solids—The Amorphous Phase," J Validation Tech., 2009, 15(3):63-68.
Berge et al., "Pharmaceutical Salts," J Pharm Sci., Jan. 1977, 66(1):1-19.
Bhidayasiri and Boonyawairoj, "Spectrum of tardive syndromes: clinical recognition and management.," Postgrad Med J, Feb. 2011, 87(1024): 132-141.
Boldt et al., "Synthesis of (+)- and (−)-Tetrabenazine from the Resolution of [alpha]-Dihydrotetrabenazine," Synthetic Communications, 2009, 39(20):3574-3585.
Brunner et al., "Comprehensive Analysis of the 16p11.2 Deletion and Null Cntnap2 Mouse Models of Autism Spectrum Disorder," PLoS One, Aug. 14, 2015, 10(8):e0134572.
Brusa et al., "Tetrabenazine improves levodopa-induced peak-dose dyskinesias in patients with Parkinson's disease," Funct. Neural., 2013, 28(2):101-5.
Bystritsky, "Treatment-resistant anxiety disorders," Mol. Psychiatry, Sep. 2006, 11(9):805-814.
Caira et al., "Crystalline Polymorphism of Organic Compounds," Topics in Current Chemistry, 1998, 198(36):163-208.
Caroff et al., "Treatment of tardive dyskinesia with tetrabenazine or valbenazine: a systematic review," J. Com. Eff. Research, 2017, 7(2):135-148.
Chinese Office Action in Chinese Application No. 201580023821.X, dated Jun. 20, 2018, 10 pages.
Citrome, "Valbenazine for tardive dyskinesia: A systematic review of the efficacy and safety profile for this newly approved novel medication—What is the number needed to treat, number needed to harm and likelihood to be helped or harmed?," Int J Clin Pract., 2017, e12964.
Cohen-Mansfield et al., "A description of agitation in a nursing home," J Gerontol., May 1989, 44(3):M77-M84.
Correll and Schenk, "Tardive dyskinesia and new antipsychotics," Curr Opin Psychiatry, Mar. 2008, 21(2):151-156.
Corvin, "Two patients walk into a clinic . . . a genomics perspective on the future of schizophreniam," BMC Biol., 2011, 8 pages.
Cummings et al., "The Neuropsychiatric Inventory: comprehensive assessment of psychopathology in dementia," Neurology, 1994, 44:2308-2314.
Derangula et al, "Liquid chromatography-tandem mass spectrometric assay for the determination of tetrabenazine and its active metabolites in human plasma: a pharmacokinetic study," Biomedical Chromatography, Jun. 2013, 27(6):792-801.
Drug Development and Drug Interactions: Table of Substrates, Inhibitor and Inducers at https://www.fda.gov/drugs/developmentapprovalprocess/developmentesources/druginteractionslabeling/ucm093664.htm, U.S. Food and Drug Administration, 2017, 18 pages.
Erickson et al., "Reserpine- and tetrabenazine-sensitive transport of (3)H-histamine by the neuronal isoform of the vesicular monoamine transporter," Journal of Molecular Neuroscience, 1995, 6(4):277-287.
Eurasian Office Action in Eurasian Application No. 201890108, dated Oct. 30, 2018, 5 pages.
European Office Action in European Application No. 15734438.5, dated Jul. 17, 2018, 4 pages.
Extended European Search Report in European Appln. No. 16734150.2, dated Apr. 11, 2019, 7 pages.
Fahr, "Kapseln," Pharmazeutische Technologie, Jan. 2000, p. 237.
Fields et al., "Pill Properties that Cause Dysphagia and Treatment Failure," Current Therapeutic Research, Aug. 2015, 77:79-82.
Foster et al., "Deuterium isotope effects in the metabolism of drugs and xenobiotics: implications for drug design," Adv Drug Res., 1985, 14:1-36.

(56) References Cited

OTHER PUBLICATIONS

Gantois et al., "Restoring the phenotype of fragile X syndrome: insight from the mouse model," Curr Mol Med., Sep. 2001, 1(4):447-455.
Gately et al., "Deuterioglucose: alteration of biodistribution by an isotope effect," J Nucl Ned., 1986, 27(3):388-394.
Gordon et al., "The metabolism of the abortifacient terpene, (R)-(+)-pulegone, to a proximate toxin, menthofuran," Drug Metab Disp., 1987, 15(5):589-594.
Gottlieb et al., "NMR Chemical Shifts of Common Laboratory Solvents as Trace Impurities," J. Org. Chem. 1997, 62 (21): 7512-7515.
Grigoriadis et al., "Pharmacologic characterization of valbenazine (NBI-98854) and its metabolites," Journal of Pharmacology and Experimental Therapeutics, 2017, 361(3):454-461.
Guilloteau et al., "PET and SPECT exploration of central monoaminergic transporters for the development of new drugs and treatments in brain disorders," Current Pharmaceutical Design, Jan. 1, 2005, 11(25):3237-3245.
Gulieva et al., "Neuropharmacology analysis of the effect of olanzapine and clozapine on behavior characteristics and neuromodulator content in rat brain structure," Psychopharmacology and biological necrology, 2004, 585-589.
Guridi et al., "Clinical Features, Pathophysiology, and Treatment of Levodopa-Induced Dyskinesias in Parkinson's Disease," Parkinson's Disease, 2012, 1-15.
Harriot et al., "Identification of the First Selective Small Molecule BB2 Antagonists," Poster, Presented at the 249th ACS National Meeting & Exposition, Denver CO, Mar. 22-26, 2015, 1 page.
Hauser et al., "KINECT 3: A phase 3 randomized, double-blind, placebo-controlled trial of valbenazine for tardive dyskinesia," Americal Journal of Psychiatry, 2016, 174(5):476-484.
Healy et al., "Clozapine-reserpine combination for refractory psychosis," Schizophrenia Research, Jan. 1, 1997, 25:259-260.
Herrmann et al., "A Placebo-Controlled Trial of Valproate for Agitation and Aggression in Alzheimer's Disease," Dement Geriatr Cogn Disord., Jan. 2007, 23:116-119.
Hoare et al., "Conformational states of the corticotropin releasing factor 1 (CRF1) receptor: detection, and pharmacological evaluation by peptide ligands," Peptides, Dec. 2003, 24(12):1881-1897.
Horev et al., "Dosage-dependent phenotypes in models of 16p11.2 lesions found in autism," Proc Natl Acad Sci USA., 2011, 108(41):17076-17081.
Howard et al., "Guidelines for the management of agitation in dementia," Int. J. Geriatr. Psychiatry, Jul. 2001, 16(7):714-717.
Hu, "New Fluorescent Substrate Enables Quantitative and High-throughput Examination of Vesicular Monoamine Transporter 2 (VMAT2)," ACS Chem Biol. Sep. 20, 2013:8(9):1947-1954.
Ingrezza, Highlights of Prescribing Information, Neurocrine Biosciences, Inc., revised Oct. 2017, 15 pages.
Ingrezza, Patient Information, Neurocrine Biosciences, Inc., revised Oct. 2017, 1 page.
Ingrezza, Highlights of Prescribing Information, Neurocrine Biosciences, Inc., published Apr. 9, 2020, 19 pages.
Ingrezza, Highlights of Prescribing Information, Neurocrine Biosciences, Inc., published Aug. 10, 2018, 17 pages.
Ingrezza, Highlights of Prescribing Information, Neurocrine Biosciences, Inc., published Jul. 15, 2019, 17 pages.
International Preliminary Report on Patentability in Appln. No. PCT/US2017/055907, dated Apr. 14, 2020, 18 pages.
International Preliminary Report on Patentability in Appln. No. PCT/US2017/055947, dated Apr. 23, 2020, 10 pages.
International Preliminary Report on Patentability in Appln. No. PCT/US2018/029255, dated Oct. 29, 2019, 7 pages.
International Preliminary Report on Patentability in International Application No. PCT/US2016/039098, dated Dec. 26, 2017, 8 pages.
International Preliminary Report on Patentability in International Application No. PCT/US2017/055877, dated Jul. 30, 2019, 11 pages.
International Preliminary Report on Patentability in International Application No. PCT/US2017/055931, dated Jul. 30, 2019, 16 pages.
International Preliminary Report on Patentability in International Application No. PCT/US2017/055965, dated Jul. 30, 2019, 8 pages.
International Preliminary Report on Patentability in International Application No. PCT/US2017/055980, dated Jul. 30, 2019, 7 pages.
International Preliminary Report on Patentability in International Appln. No. PCT/US2017/064196, dated Jun. 4, 2019, 6 pages.
International Report on Patentability in International Application No. PCT/US2015/029519, dated Nov. 8, 2016, 8 pages.
International Search Report and Written Opinion in Appln. No. PCT/US2017/055877, dated Dec. 26, 2019, 11 pages.
International Search Report and Written Opinion in Appln. No. PCT/US2017/055907, dated Dec. 5, 2017, 21 pages.
International Search Report and Written Opinion in Appln. No. PCT/US2017/055931, dated Dec. 11, 2017, 17 pages.
International Search Report and Written Opinion in Appln. No. PCT/US2017/55965, dated Dec. 5, 2017, 9 pages.
International Search Report and Written Opinion in Appln. No. PCT/US2018/029255, dated Jun. 26, 2018, 9 pages.
International Search Report and Written Opinion in Appln. No. PCT/US2017/55980, dated Dec. 1, 2017, 9 pages.
International Search Report and Written Opinion in International Application No. PCT/US2015/029519, dated Jun. 21, 2015, 11 pages.
International Search Report and Written Opinion in International Application No. PCT/US2016/039098, dated Nov. 22, 2016, 15 pages.
International Search Report and Written Opinion in International Appln. No. PCT/US2017/064196, dated Feb. 21, 2018, 10 pages.
International Search Report and Written Opinion in International Appln. No. PCT/US2019/46462, dated Nov. 7, 2019, 14 pages.
International Search Report in Appln. No. PCT/US2017/055947, dated Dec. 5, 2017, 8 pages.
Jacq et al., "Development and validation of an automated static headspace gas chromatography-mass spectrometry (SHS-GC-MS) method for monitoring the formation of ethyl methane sulfonate from ethanol and methane sulfonic acid," J Pharm. Biomed Anal., 2008, 48(5):1339-1344.
Jankovic and Beach, "Long-term effects of tetrabenazine in hyperkinetic movement disorders," Neurology, Feb. 1, 1997, 48(2):359-362.
Jankovic et al., "Lesch-Nyhan Syndrome. A Study of Motor Behaviour and Cerebrospinal Fluid Neurotransmitters," Ann Neuro., May 1988, 23(5):466-469.
Jankovic., "Dopamine depleters in the treatment of hyperkinetic movement disorders," Expert Opinion on Pharmacotherapy, 17.18, 2016, 2461-2470.
Japanese Office Action in Japanese Application No. 2016-566238, dated Feb. 12, 2019, 13 pages.
Jiang, "Application of Deuteration in Drug Research," Qilu Pharmacautical Affairs, 29(11):682-684.
Jinnah et al., "Amphetamine-induced behavioral phenotype in a hypoxanthine-guanine phosphoribosyltransferase-deficient mouse model of Lesch-Nyhan syndrome," Behav Neurosci., Dec. 1991, 105(4):1004-1012.
Josiassen et al., "Long-term safety and tolerability of valbenazine (NBI-98854) in subjects with tardive dyskinesia and a diagnosis of Schizophrenia or mood disorder," Psychopharmacology Bulletin, 2017, 47(3):61-68.
Jul et al., "Hyperactivity with Agitative-Like Behavior in a Mouse Tauopathy Model," J Alzheimer's Dis., 2015, 49(3):783-795.
Katz et al., "Preclinical research in Rett syndrome: setting the foundation for translational success," Disease Models & Mechanisms, 2012, 5:733-745.
Kay et al., "The Positive and Negative Syndrome Scale (PANSS) for Schizophrenia," Schizophrenia Bulletin, 1987, 13:262-276.
Kazdoba et al., "Modeling fragile X syndrome in the Fmr1 knockout mouse," Intractable Rare Dis Res., Nov. 2014, 3(4):118-133.
Kenney et al., "Long-Term Tolerability of Tetrabenazine in the Treatment of Hyperkinetic Movement Disorders," Movement Disorders, 2007, 22(2):193-197.

(56) References Cited

OTHER PUBLICATIONS

Kenney et al., "Tetrabenazine in the treatment of hyperkinetic movement disorders," Expert Review Neurotherapeutics, 2006, 6(1):7-17.
Khalsa et al., "Treatment-resistant OCD: Options beyond first-line medications," Curr. Psychiatry, 2011, 10(11):45-52.
Kilbourn et al., "Absolute configuration of (+)-alpha-dihydrotetrabenazine, an active metabolite of tetrabenazine," Chiralty, 1997, 9:(1)59-62.
Kilbourn et al., "Binding of alpha-dihydrotetrabenazine to the vesicular monoamine transporter is stereospecific," Eur J Pharmacol May 24, 1995, 278(3):249-252.
Kilbourn et al., "In vivo binding of (+)-alpha-[3H]dihydrotetrabenazine to the vesicular monoamine transporter of rat brain: bolus vs. equilibrium studies," European Journal of Pharmacology, 1997, 331(2-3):161-168.
Kilbourn et al., "In vivo measures of dopaminergic radioligands in the rat brain: equilibrium infusion studies," Synapse, Mar. 1, 2002, 43(3):188-194.
Kim, "Valbenazine: First Global Approval," Drugs, 2017, 77:1123-1129.
Kimiagar er al., "Rapid improvement of tardive dyskinesia with tetrabenazine, clonazepam and clozapine combined: a naturalistic long-term follow-up study," J Neurol., Nov. 9, 2011, 259(4):660-664.
Koch et al., "Successful Therapy of Tardive Dyskinesia in a 71-year-old Woman with a combination of Tetrabenazine, Olanzapine and Tiapride," IJCP, Mar. 1, 2003, 57(2):147-149.
Kuehn et al., "A potential animal model for Lesch-Nyhan syndrome through introduction of HPRT mutations into mice," Nature,Mar. 1987, 326(6110):295-298.
Kurlan, "Treatment of Tourette Syndrome," Neurotherapeutics, 2014, 11:161-165.
Kushner et al., "Pharmacological uses and perspectives of heavy water and deuterated compounds," Can J Physiol Pharmacol., 1999, 77(2):79-88.
Lee et al., "In vitro and in vivo studies of benzisoquinoline ligands for the brain synaptic vesicle monoamine transporter," J. Med Chem., Jan. 5, 1996, 39(1):191-196.
Lijinsky et al., "Dose-response studies in carcinogenesis by nitroso-N-methyl-N-(2-phenyl)ethylamine in rats and the effects of deuterium substitution," Food Cosmet. Toxicol., Aug. 1982, 20(4):393-399.
Lijinsky et al., "Dose-response studies with nitrosoheptamethyleneimine and its alpha-deuterium-labeled derivative in F344 rats," J Natl Cancer Inst., Nov. 1982, 69(5):1127-1133.
Loewen et al., "Evaluation of the potential for concomitant medications to affect valbenazine pharmacokinetics," Poster, Presented at the American Society of Clinical Psychopharmacology, May 29-Jun. 2, 2017: Miami, FL, 1 page.
Loewen et al., "Evaluation of the potential for valbenzaine to elicit drug interactions," Poster, Presented at The American Society of Clinical Psychopharmacology, May 29-Jun. 2, 2017: Miami, FL, 1 page.
Lombroso et al., "Tourette Syndrome and Obsessive-Compulsive Disorder ," Brain Dev., 2008, 30(4): 231-237.
Loriot et al., "Drug insight: gastrointestinal and hepatic adverse effects of molecular-targeted agents in cancer therapy," Nature Clinical Practice Oncology, 2008, 5(5):268-278.
Luo et al., "Single dose and repeat once-daily dose safety, tolerability, and pharmacokinetics of valbenazine in healthy male subjects," Poster, Presented at The American Psychiatric Association Annual Meeting, May 20-24, 2017, San Diego, CA, 1 page.
Madan, Invited Speaker, "NBI-98854. Human pharmacokinetics of NBI-98854 a selective inhibitory of VMAT2 with an attractive PK and safety profile for hyperkinetic movement disorders," Pipeline Projects Session, 12th annual meeting of American Society for Experimental NeuroTherapeutics, Bethesda, MD, 2010, 5 slides.
Madan, Invited Speaker, "NBI-98854: Selective inhibitor of VMAT2 with an attractive PK and safety profile for hyperkinetic movement disorders," Pipeline Projects Session, 11th annual meeting of American Society for Experimental NeuroTherapeutics, Arlington, VA, 2009, 9 slides.
Mangold et al., "Effects of deuterium labeling on azido amino acid mutagenicity in *Salmonella typhimurium*," Mutation Res., 1994, 308(1):33-42.
Marder et al., "Kinect 3: a randomized, double-blind, placebo-controlled phase 3 trial of valbenazine (NBI-98854) for Tardive Dyskinesia," American Academy of Neurology, 2016, 9 pages.
Margolese et al., "Tardive dyskinesia in the era of typical and atypical antipsychotics. Part 1: pathophysiology and mechanisms of induction," Can J Psychiatry, Aug. 2005, 50(9):541-47.
Material Safety Data Sheet. Product Name Valbenazine tosylate. Published May 1, 2014 (see Revision date). Retrieved from internet May 23, 2020. URL: https://www.selleckchem.com/msds/MSDS_S9500.pdf.
McBride et al., "Using *Drosophila* as a tool to identify Pharmacological Therapies for Fragile X Syndrome," Drug Discov Today Technol., Sep. 24, 2012, 10(1):e129-e136.
Mehvar et al., "Pharmacokinetics of tetrabenazine and its major metabolite in man and rat. Bioavailability and dose dependency studies," Drug Metabolism and Distribution, 1987, 15(2):250-255.
mentalhealthamerica.net [online], "Depression," [retrieved on Dec. 17, 2018], retrieved from URL<http://www.mentalhealthamerica.net/conditions/depression>, 3 pages.
Mineur et al., "Social behavior deficits in the Fmr1 mutant mouse," Behav Breain Res., Mar. 15, 2006, 168(1):172-175.
Muller et al., "Valbenazine for the treatment of tardive dyskinesia," Expert Review of Neurotherapeutics, 2017, 17(2):1135-1144.
Muller, "Valbenazine granted breakthrough drug status for treating tardive dyskinesia," Expert Opin Investig Drugs, 2015, 24(6):737-42.
Near, "[3H]Dihydrotetrabenazine binding to bovine striatal synaptic vesicles," Mol. Pharmacol., Sep. 1986, 30:252-257.
Nikoloff et al., "Association between CYP2D6 genotype and tardive dyskinesia in Korean schizoprenics," The Pharmacogenomics J, 2002, 2:400-407.
ninds.nih.gov [online], Available on or before Jan. 24, 2013, via Internet Archive: Wayback Machine URL <https://web.archive.org/web/20130124115120/www.ninds.nih.gov/disorders/rett/detail_rett.htm>, retrieved on Dec. 17, 2018], retrieved from URL<www.ninds.nih.gov/disorders/rett/detail_rett.htm>, 6 pages.
Nunes et al., "Effort-related motivational effects of the VMAT-2 inhibitor tetrabenazine: implications for animal models of the motivational symptoms of depression," J. Neurosci., 2013, 33(49):19120-30.
Nyhan et al., "Lesch-Nyhan Syndrome," Posted Sep. 25, 2000[last update May 15, 2014], 21 pages.
O'Brien et al., "NBI-98854, a selective monoamine transport inhibitor for the treatment of tardive dyskinesia: a randomized, double-blind, placebo-controlled study," Movement Disorders, 2015, 30(12):1681-1687.
Ondo et al, "Tetrabenazine treatment for tardive dyskinesia: assessment by randomized videotape protocol," Am J Psychiatry, Aug. 1999, 156(8):1279-1281.
Owesson-White et al., "Sources contributing to the average extracellular concentration of dopamine in the nucleus accumbens," J Neurochem., 2012, 121:252-62.
Pallanti and Quercioli, "Treatment-refractory obsessive-compulsive disorder: methodological issues, operational definitions and therapeutic lines," Neuropsychopharmacol. Biol Psychiatry, May 2006, 30(3):400-412.
PCT International Preliminary Report on Patentability in International Appln. No. PCT/US2018/051579, dated Apr. 2, 2020, 25 pages.
PCT International Search Report and Written Opinion in International Appln. No. PCT/US2018/051579, dated Mar. 18, 2019, 36 pages.
Piccinni et al., "Effectiveness of a Clozapine-Aripiprazole Combination in Tourette Syndrome and Bipolar Spectrum Disorder," J Neuropsychiatry Clin Neurosci., Jan. 1, 2013, 25:1.
Pincus, "Management of digoxin toxicity," Aust. Prescr., 2016, 39(1):18-21.

(56) References Cited

OTHER PUBLICATIONS

Pittenger et al., "Pharmacological treatment of obsessive-compulsive disorder," Psychiatr. Clin. North Am., 2014, 37(3):375-391.
Poliak et al., "Juxtaparanodal clustering of Shaker-like K+ channels in myelinated axons depends on Caspr2 and TAG-1," J Cell Biol., Sep. 15, 2003, 162(6):1149-1160.
Porta et al., "Tourette's syndrome and role of tetrabenazine," Clin Drug Invest., 2008, 28(7):443-459.
Portman et al., "Behavioral abnormalities and circuit defects in the basal ganglia of a mouse model of 16p11.2 deletion syndrome," Cell Rep., May 22, 2014, 7(4):1077-1092.
Prescott, "Powder handling," Pharmaceutical Process Scale-Up, Jan. 2011, 195-209.
Provenzano et al., "Mutant mouse models of autism spectrum disorders," Dis. Markers, 2012, 33(5):225-239.
Rao et al, "Review article: metoclopramide and tardive dyskinesia," Aliment Pharmacol Ther 2010, 31(1):11-19.
Remington et al., "Tetrabenazine Augmentation in Treatment-Resistant Schizophrenia," Journal of Clinical Psychopharmacology, Feb. 1, 2012, 32(1):95-99.
Robey et al., "Modes and patterns of self-mutilation in persons with Lesch-Nyhan disease," Dev Med Child Neurol. Mar. 2003, 45(3):167-171.
Russian Office Action in Russian Application No. 2016147523, dated Dec. 27, 2018, 18 pages.
Sakimoto et al., "Phenotypic abnormalities in a chorea-acanthocytosis mouse model are modulated by strain background," Biochem Biophys Res Commun., 472(1):118-124.
Santus and Baker, "Osmotic drug delivery: a review of the patent literature," J. Controlled Release, 1995, 35(1)1-21.
Sawant, "Necessity of Establishing Chemical Integrity of Polymorphs of Drug Substance Using a Combination of NMR, HPLC, Elemental Analysis, and Solid-State Characterization Techniques: Case Studies," Organic Process Research & Development 17.3, 2013, :519-532.
Scherman et al., "[3H]dihydrotetrabenazine, a new in vitro monoaminergic probe for human brain," Journal of Neurochemistry 1988, 50(4):1131-1136.
Schneider et al., "Efficacy and adverse effects of atypical antipsychotics for dementia: meta-analysis of randomized, placebo-controlled trials," Am J Geritr Psychiatry., 2006, 14(3):191-210.
Schretlen et al., "Behavioral aspects of Lesch-Nyhan disease and its variants," Dev Med Child Neurol., Oct. 2005, 47(10):673-677.
Schretlen et al., "Neurocognitive functioning in Lesch-Nyhan disease and partial hypoxanthine-guanine phosphoribosyltransferase deficiency," J Int. Neuropsychol Soc., 2001, 7:805-812.
Scott et al., Making and Breaking Serotonin Neurons and Autism, Int J Devi Neuroscience., 2005, 23:277-285.
Sever et al., "Process Analytical Technology in Solid Dosage Development and Manufacturing," Developing Solid Oral Dosage Forms Pharmaceutical Theory and Practice, Jan. 2008, 827-841.
Shen et al. "Safety and Efficacy of Tetrabenazine and use of Cocomitant Medications during Long-Term, Open-Label Treatment of Chorea Associated with Huntington's and Other Diseases," Tremor and Other Myperkinetic Movements, Oct. 22, 2013, https://tremorjournal.org/index.php/tremor/article/view/191, pp. 1-12.
Silverman et al., "Behavioural phenotyping assays for mouse models of autism," Nature Reviews Neuroscience, Jul. 2010, 11(7):490-502.
Simpson et al., "A rating scale for extrapyramidal side effects," Acta Psychiatry Scand Suppl, 1970, 212:11-19 .
Skor et al., "Differences in dihydrotetrabenazine isomer concentrations following administration of tetrabenazine and valbenazine," Drugs R D, 2017, 17:449-459.
Smolders et al., "Pharmacokinetics, efficacy, and safety of Hepatitis C virus drugs in patients with liver and/or renal impairment," Drug safety, 2016, 39(7):589-611.
Solon, "Risperidone-reserpine combination in refractory psychosis," Schizophrenia Research, Dec. 1, 1996, 22(3):265-266.

Spencer et al., "Social behavior in Fmr1 knockout mice carrying a human FMR1 transgene," Behave Neurosci., Jun. 2008, 122(3):710-715.
Spina et al., "Effect of fluoxetine on the plasma concentrations of clozapine and its major metabolites in patients with schizophrenia," International Clinical Psychopharmacology, May 1, 1998, 13(3):141-145.
STN CAS RN: 1639208-54-0, entered STN Dec. 22, 2014, 1 page.
Sun et al., "Preparation and evaluation of tetrabenazine enantiomers and all eight stereoisomers of dihydrotetrabenazine as VMAT2 inhibitors," Eur. J. Med. Chem, 2011, 46(5): 1841-1848
Table 14.3.5.14.1, "Young Mania Rating Scale (YMRS) Total Score and Change from Baseline (CFB) Values by Visit and Treatment Group," Neurocrine Biosciences, Inc., Oct. 8, 2015, 6 pages.
Tandon et al., "World Psychiatric Association Pharmacopsychiatry Section Statement on Comparative Effectiveness of Antipsychotics in the Treatment of Schizophrenia," Schizophrenia Research, Mar. 1, 2008, 100(1-3):20-38.
Tarsy and Baldessarini, "Epidemiology of tardive dyskinesia: is risk declining with modern antipsychotics?" Movement Disorders, May 2006, 21(5):589-598.
Tauber et al., "Elevated Levels of the Vesicular Monoamine Transporter and a Novel Repetitive Behavior in the *Drosophila* Model of Fragile X Syndrome," PLOS ONE, Nov. 11, 6(11):e27100.
Teasdale et al., "Mechanism and Processing Parameters Affecting the Formation of Methyl Methanesulfonate from Methanol and Methanesulfonic Acid: An Illustrative Example for Sulfonate Ester Impurity Formation," Org Process Res. Dev., 2009, 15:13429-433.
Teasdale, "Sulfonate Esters—How Real is the Risk? Summary of Key Findings from PQRI Studies of the Reaction Between Sulfonic acids and Alcohols," 42 pages.
Teasdale, "Sulphonate esters: a real or imagined risk? PQRI studies to determine actual risk," British Pharmaceutical Conference, Manchester Sep. 10-12, 2007, J Pharmacy Pharmacol. A-78, Abstract 218.
Tenback et al, "Incidence and persistence of tardive dyskinesia and extrapyramidal symptoms in schizophrenia," J Psychopharmacol, Jul. 2010, 24(7):1031-1035.
Teng et al., "Lobeline displaces [3H]dihydrotetrabenazine binding and releases [3H]dopamine from rat striatal synaptic vesicles: comparison with d-amphetamine," J Neurochem. 1998, 71(1):258-265.
Thai-Curato et al., "Cardiovascular profile of valbenazine: analysis of pooled dated from three randomized, double-blind, placebo-controlled trials," Drug Safety, 2017, 41(4):429-440.
Tian et al., "CYP3A4-mediated pharmacokinetic interactions in cancer therapy," Curr. Drug Metab., 2014, 15(8):808-17.
Tomemori et al., "A gene-targeted mouse model for chorea-acanthocytosis," J Neurochem, 2005, 92(4):759-766.
Traynor, "Valbenazine approved for treatment of tardive dyskinesia," ASHP, Apr. 17, 2017, retrieved from URL: https://www.ashp.org/news/2017/04/17/valbenazine-approved-for-treatment-of-tardive-dyskinesia?loginreturnUrl=SSOCheckOnly, retrieved on Jun. 22, 2020, 3 pages.
Tsoussis et al., "Disclosure of cancer diagnosis: the Greek experience," JBUON, Open Access Journal aimed at the rapid diffusion of scientific knowledge in Oncology, 2013, 18(2):516-526.
United States Pharmacopoeia ("USP"), "Bulk Density and Tapped Density of Powders," <616>, 2015, 3 pages.
United States Pharmacopoeia ("USP"), "Disintegration," <701>, 2016, 4 pages.
United States Pharmacopoeia ("USP"), "Dissolution," <711>, 2011, 8 pages.
United States Pharmacopoeia ("USP"), "Uniformity of Dosage Units," <905>, 2016, 9 pages.
United States Pharmacopoeia, "Light Diffraction Measurement of Particle Size," <429>, 2016, 8 pages.
US Department of Health and Human Services, and Food and Drug Administration, "Size, Shape, and Other Physical Attributes of Generic Tablets and Capsules," Jun. 2015, 10 pages.
Verkerk et all., "Identification of a gene (FMR-1) containing a CGG repeat coincident with a breakpoint cluster region exhibiting length variation in fragile X syndrome," Cell, May 1991, 65(5):905-914.

(56) References Cited

OTHER PUBLICATIONS

Verma et al., "Formulation aspects in the development of osmotically controlled oral drug delivery systems," J. Controlled Release, Feb. 19, 2002, 79(1-3):7-27.
Verma et al., "Osmotically controlled oral drug delivery," Drug Development and Industrial Pharmacy, Jul. 2000, 26(7):695-708.
Wade, "Deuterium isotope effects on noncovalent interactions between molecules," Chem Biol Interact., Feb. 1999, 117(3):191-217.
Watts et al., "Clinical and biochemical studioes on treatment of Lesch-Nylan Syndrome," Archives of Disease in Childhood., 1974, 49:693-702.
Weihe and Eiden, "Chemical neuroanatomy of the vesicular amine transporters.," The FASEB Journal, Dec. 2000, 14(15):2435-2449.
Woods et al, "Incidence of tardive dyskinesia with atypical versus conventional antipsychotic medications: a prospective cohort study," J Clin Psychiatry, Apr. 2010, 71(4):463-474.
Yamashita et al., "Modeling of rifampicin-induced CYP3A4 activation dynamics for the prediction of clinical drug-drug interactions in vitro data," PLoS One, 2013, 8(9):e70330, 11 pages.
Yasumoto et al., "Inhibitory effect of selective serotonin reuptake inhibitors on the vesicular monoamine transporter 2," Neuroscience Letters, May 1, 2009, 454(3):229-232.
Zello et al., "Plasma and urine enrichments following infusion of L[1-13C]phenylalanine and L-[ring-2H5]phenylalanine in humans. evidence for an isotope effect in renal tubular reabsorption," Metabolism, 1994, 43(4):487-491.
Zhang et al, "Synergistic Effects of Olanzapine and other Antipsychotic Agents in Combination with Fluoxetine on Norepinephrine and Dopamine release in rate Prefrontal Cortex," Neuropsychopharmacology, Sep. 1, 2000, 23(3):250-262.
U.S. Appl. No. 17/074,278, Moore Jr. et al., filed Oct. 19, 2020.
U.S. Appl. No. 17/074,383, Moore Jr. et al., filed Oct. 19, 2020.
Center for Drug Evaluation and Research Application No. 2092410 ("Publication No. 2092410"), Clinical Pharmacology and Biopharmaceuticals Review, Jun. 1, 2017.
Citrome, "Reprint of: Clinical management of tardive dyskinesia: five steps to success," Journal of Neurological Sciences, 2018, 389:61-66.
Hassan et al., "Drug use and dosing in chronic kidney disease," Annals of the Academy of Medicine, 2009, 38(12):1095-1103.
[No Author Listed], "Blenrep (belantamab mafodotin-blmf) Highlights of Prescribing Information," GlaxoSmithKline, Aug. 2020, 23 pages.
[No Author Listed], "Crestor (rosuvastatin calciu) Highlights of Prescribing Information," AstraZeneca Pharmaceuticals, May 2016, 35 pages.
[No Author Listed], "Iclusig (ponatinib) Highlights of Prescribing Information," ARIAD Pharmaceuticals, Inc., Dec. 2012, 17 pages.
[No Author Listed], "Invokana (canagliflozin), Highlights of Prescribing Information," Janssen Pharmaceuticals, Inc., Oct. 2018, 50 pages.
[No Author Listed], "Veklury (remdesivir) Highlights of Prescribing Information," Gilead Sciences, Inc., Oct. 2020, 30 pages.
[No Author Listed], "Zepzelca (lubrinectedin) Highlights of Prescribing Information," Jazz Pharmaceuticals, Inc., Jun. 2020, 16 pages.
[No Author Listed], "Zocor (simvastatin) Highlights of Prescribing Information," Merck Sharpe & Dohme Corp., Sep. 2020, 22 pages.

* cited by examiner

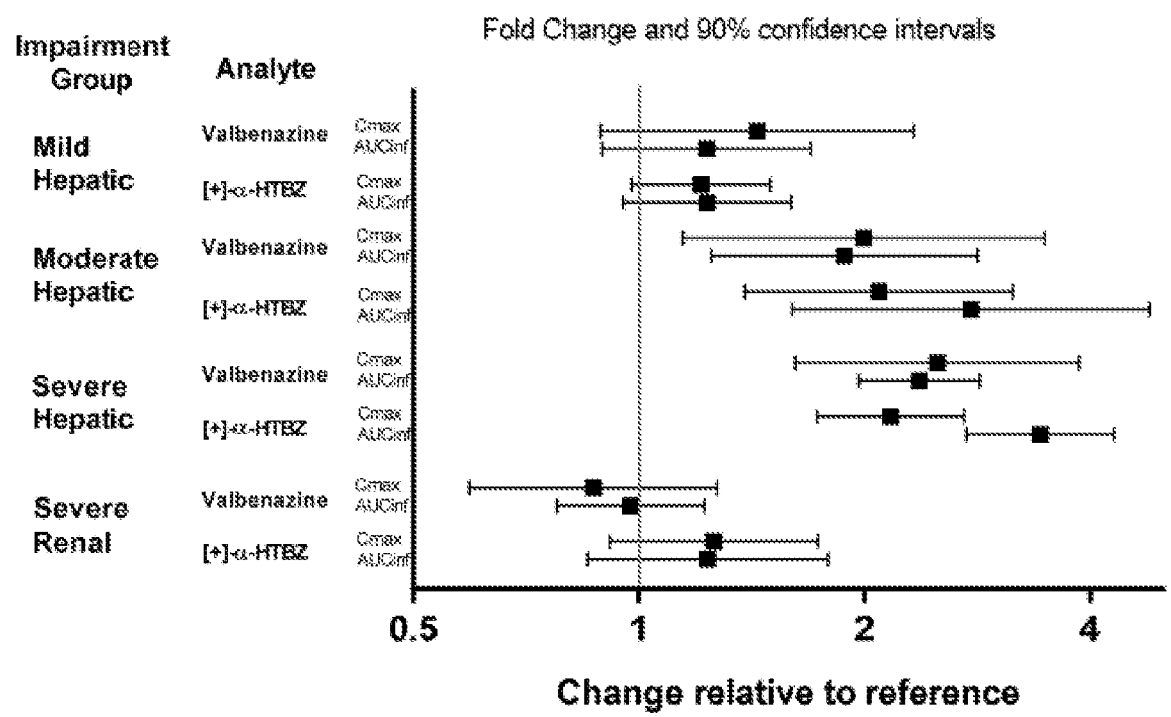

METHODS FOR THE ADMINISTRATION OF CERTAIN VMAT2 INHIBITORS

This application claims the benefit of U.S. Provisional Application No. 62/890,697, filed Aug. 23, 2019 and U.S. Provisional Application No. 63/028,754, filed May 22, 2020, which are incorporated herein by reference for all purposes.

Dysregulation of dopaminergic systems is integral to several central nervous system (CNS) disorders, including neurological and psychiatric diseases and disorders. These neurological and psychiatric diseases and disorders include hyperkinetic movement disorders, and conditions such as schizophrenia and mood disorders. The transporter protein vesicular monoamine transporter-2 (VMAT2) plays an important role in presynaptic dopamine release and regulates monoamine uptake from the cytoplasm to the synaptic vesicle for storage and release.

Despite the advances that have been made in this field, there remains a need for new therapeutic products useful to treatment of neurological and psychiatric diseases and disorders and other related diseases or conditions described herein. One such agent is valbenazine, which has the following chemical structure:

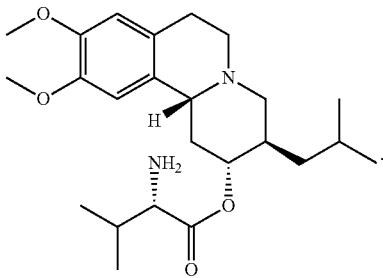 [SMILES: COc1cc2c(cc1OC)[C@H]1C[C@@H](OC(=O)[C@@H](N)C(C)C)[C@H](CC(C)C)CN1CC2]

A formulation of the VMAT2 inhibitor, valbenazine:4-toluenesulfonate (1:2) (referred to herein as "valbenazine ditosylate") has been previously reported in the FDA approved drug label INGREZZA©, which was approved in the United States on 11 Apr. 2017 for the treatment of adults with tardive dyskinesia (TD). The prescribing information for INGREZZA indicates that INGREZZA was not recommended in patients with severe renal impairment (creatinine clearance <30 mL/min).

There is a significant, unmet need for methods of administering a VMAT2 inhibitor, such as valbenazine, or a pharmaceutically acceptable salt and/or isotopic variant thereof, to a patient, particularly to a patient with severe renal impairment, in need thereof. The present disclosure fulfills these and other needs, as evident in reference to the following disclosure.

SUMMARY

Provided is a method of administering a vesicular monoamine transporter 2 (VMAT2) inhibitor to a subject in need thereof, wherein the subject has severe renal impairment, comprising: administering the VMAT2 inhibitor to the subject in need thereof.

Also provided is a method of administering a vesicular monoamine transporter 2 (VMAT2) inhibitor to a subject in need thereof, comprising: administering the VMAT2 inhibitor to the subject in need thereof, subsequently determining that the subject has severe renal impairment, and continuing administration of the VMAT2 inhibitor.

Also provided is a method of administering a vesicular monoamine transporter 2 (VMAT2) inhibitor to a subject in need thereof, wherein the subject has mild or moderate renal impairment, comprising: administering the VMAT2 inhibitor to the subject in need thereof, subsequently determining that the subject has severe renal impairment, and continuing administration of the VMAT2 inhibitor.

Also provided is a method of treating a disease or disorder requiring a vesicular monoamine transporter 2 (VMAT2) inhibitor in a subject in need thereof, wherein the subject has severe renal impairment, comprising: administering the VMAT2 inhibitor to the subject in need thereof.

Also provided is a method of treating a neurological or psychiatric disease or disorder in a subject in need thereof, comprising: administering a vesicular monoamine transporter 2 (VMAT2) inhibitor to the subject in need thereof, wherein the subject has severe renal impairment.

In some embodiments, the VMAT2 inhibitor is chosen from (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester and pharmaceutically acceptable salts and/or isotopic variants thereof. In some embodiments, the VMAT2 inhibitor is chosen from (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester and pharmaceutically acceptable salts thereof. In some embodiments, the VMAT2 inhibitor is a tosylate salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester. In some embodiments, the VMAT2 inhibitor is a ditosylate salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester. In some embodiments, the ditosylate salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester is in crystalline Form I.

In some embodiments, the VMAT2 inhibitor is an isotopic variant that is L-Valine, (2R,3R,11bR)-1,3,4,6,7,11b-hexahydro-9,10-di(methoxy-d3)-3-(2-methylpropyl)-2H-benzo[a]quinolizin-2-yl ester or a pharmaceutically acceptable salt thereof.

In some embodiments, the VMAT2 inhibitor is tetrabenazine (9,10-dimethoxy-3-isobutyl-1,3,4,6,7,11b-hexahydro-2H-pyrido[2,1-a]isoquinolin-2-one), or a pharmaceutically acceptable salt and/or isotopic variant thereof. In some embodiments, tetrabenazine is chosen from the RR, SS, RS, and SR isomers of tetrabenazine, and mixtures thereof. In some embodiments, tetrabenazine is a mixture of the RR and SS isomers.

In some embodiments, the VMAT2 inhibitor is deutetrabenazine.

In some embodiments, the VMAT2 inhibitor is chosen from dihydrotetrabenazine (2-hydroxy-3-(2-methylpropyl)-1,3,4,6,7,11b-hexahydro-9,10-dimethoxy-benzo(a)quinolizine), or a pharmaceutically acceptable salt and/or isotopic variant thereof. In some embodiments, dihydrotetrabenazine is chosen from the RRR, SSS, SSRR, RSS, SSR, RRS, RSR, and SRS isomers of dihydrotetrabenazine, and mixtures thereof. In some embodiments, the VMAT2 inhibitor is the RRR isomer ((+)-α-3-isobutyl-9,10-dimethoxy-1,3,4,6,7,11b-hexahydro-2H-pyrido[2,1-a]isoquinolin-2-ol), or a pharmaceutically acceptable salt and/or isotopic variant thereof.

These and other aspects of the invention will be apparent upon reference to the following detailed description. To this end, various references are set forth herein which describe in more detail certain background information, procedures, compounds, and/or compositions, and are each hereby incorporated by reference in their entirety.

BRIEF DESCRIPTION OF THE FIGURE

FIG. 1 depicts the effects of hepatic impairment and severe renal impairment on valbenazine pharmacokinetics.

DETAILED DESCRIPTION

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" or "some embodiments" or "a certain embodiment" means that a particular feature, structure or characteristic described in connection with the embodiment is included in at least one embodiment. Thus, the appearances of the phrases "in one embodiment" or "in an embodiment" or "in some embodiments" or "in a certain embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise.

As used herein, "valbenazine" may be referred to as (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester; or as L-Valine, (2R,3R, 11bR)-1,3,4,6,7,11b-hexahydro-9,10-dimethoxy-3-(2-methylpropyl)-2H-benzo[a]quinolizin-2-yl ester or as NBI-98854 with the following structure:

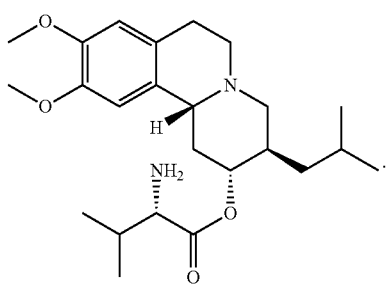 [SMILES: COc1cc2c(cc1OC)[C@H]1C[C@@H](OC(=O)[C@@H](N)C(C)C)[C@H](CC(C)C)CN1CC2]

INGREZZA contains valbenazine, present as valbenazine ditosylate salt, with the chemical name, L-Valine, (2R,3R, 11bR)-1,3,4,6,7,11b-hexahydro-9,10-dimethoxy-3-(2-methylpropyl)-2H-benzo[a]quinolizin-2-yl ester, 4-methylbenzenesulfonate (1:2). Valbenazine ditosylate is slightly soluble in water. Its molecular formula is C38H54N2O10S2, and its molecular weight is 762.97/mol (ditosylate salt) with the following structure:

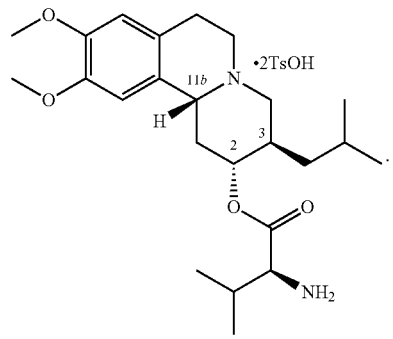 [SMILES: COc1cc2c(cc1OC)[C@H]1C[C@@H](OC(=O)[C@@H](N)C(C)C)[C@H](CC(C)C)CN1CC2]

Valbenazine ditosylate may exist as an amorphous form and crystalline Forms I-VI. The synthesis and characterization of the amorphous form and crystalline Forms I-VI of valbenzine ditosylate have been described in the U.S. Pat. No. 10,065,952, which is incorporated herein by reference in its entirety for all purposes. The crystalline Form I of valbenazine ditosylate has an X-ray diffraction pattern. The X-ray diffraction pattern of the crystalline Form I of valbenazine ditosylate may include peaks at two-theta angles of approximately 6.3, 17.9, and 19.7°. The X-ray diffraction pattern of the crystalline Form I of valbenazine ditosylate may include peaks at two-theta angles of approximately 6.3, 17.9, or 19.7°. The X-ray diffraction pattern of the crystalline Form I of valbenazine ditosylate may include peaks at two-theta angles of approximately 6.3 and 17.9°. The X-ray diffraction pattern of the crystalline Form I of valbenazine ditosylate may include a peak at two-theta angles of approximately 6.3°. The crystalline Form I of valbenazine ditosylate has an endothermic differential scanning calorimetric (DSC) thermogram. In some embodiments, crystalline Form I has a DSC thermogram comprising an endothermic event with onset temperature of about 240° C. and a peak at about 250° C.

As used herein, "tetrabenazine" may be referred to as 1,3,4,6,7,11b-hexahydro-9,1O-dimethoxy-3-(2-methylpropyl)-2H-benzo(a)quinolizin-2-one. The compound has chiral centers at the 3 and 11b carbon atoms and hence can, theoretically, exist in a total of four isomeric forms as shown below:

RR

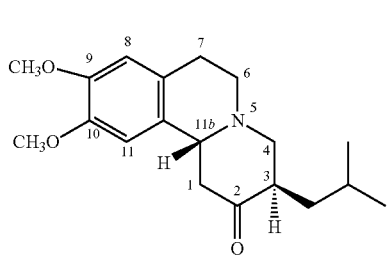

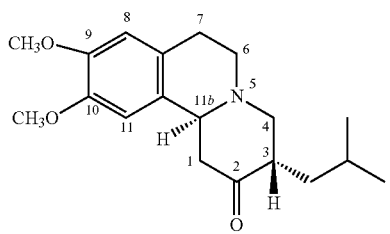

SS

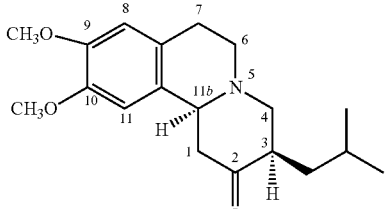

RS

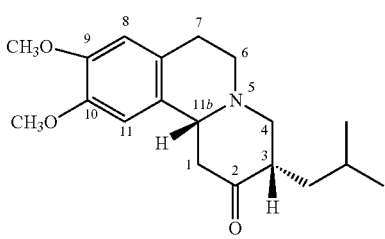

SR

Commercially available tetrabenazine is a racemic mixture of the RR and SS isomers. See, e.g., XENAZINE (tetrabenazine) US Prescribing Information, Sep. 13, 2017, which is incorporated herein by reference in its entirety for all purposes.

As used herein, "deutetrabenazine" may be referred to as (RR, SS)-1, 3, 4, 6, 7, 11b-hexahydro-9, 10-di(methoxyd3)-3-(2-methylpropyl)-2H-benzo[a]quinolizin-2-one. Deutetrabenazine is a racemic mixture containing the following compounds:

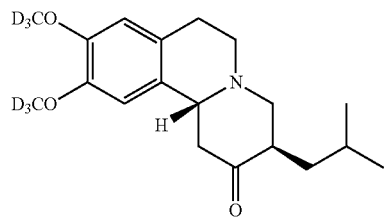

RR-Deutetrabenazine

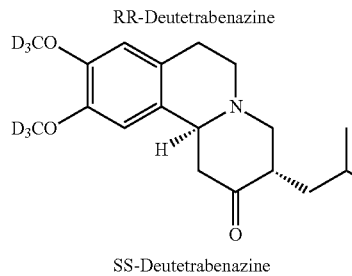

SS-Deutetrabenazine

See, e.g., AUSTEDO (deutetrabenazine) US Prescribing Information, Jun. 6, 2018, which is incorporated herein by reference in its entirety for all purposes.

As used herein, dihydrotetrabenazine may be referred to as 2-hydroxy-3-(2-methylpropyl)-1,3,4,6,7,11b-hexahydro-9,10-dimethoxy-benzo(a)quinolizine. The compound has three chiral centers and hence can, theoretically, exist in a total of eight isomeric forms as shown below:

RRR

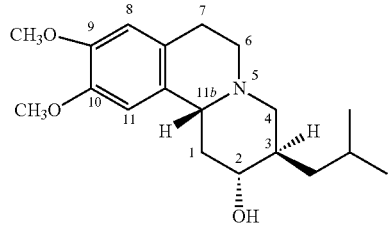

SSS

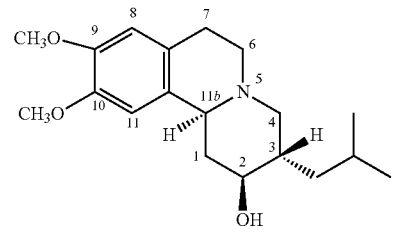

SRR

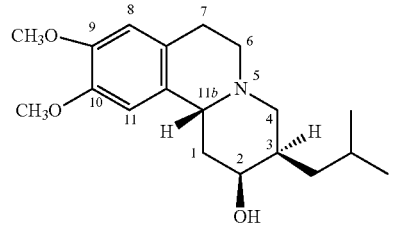

RSS

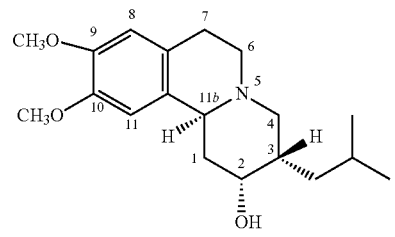

SSR

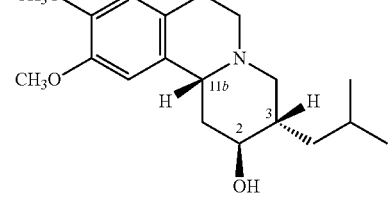

RRS

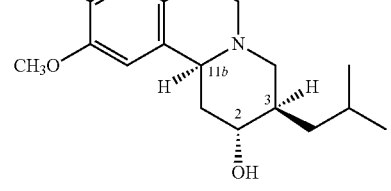

-continued

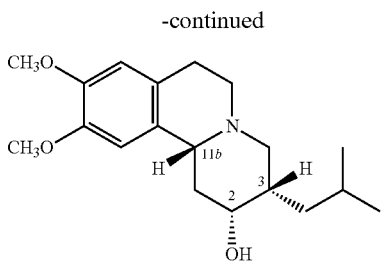
RSR

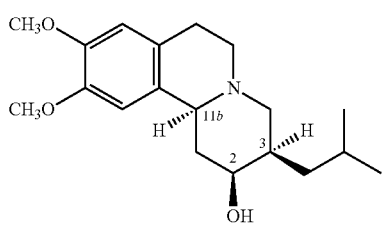
SRS

The synthesis and characterization of the eight isomers is described by Sun et al. (2011) Eur. J. Med. Chem. 1841-1848, which is incorporated herein by reference in its entirety for all purposes.

As used herein, "(+)-α-HTBZ" means the compound which is an active metabolite of valbenazine having the structure.

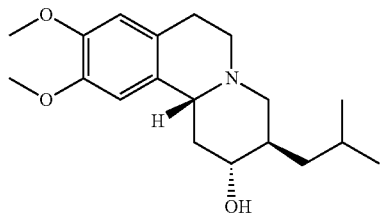 [SMILES: COc1cc2c(cc1OC)[C@H]1C[C@@H](O)[C@H](CC(C)C)CN1CC2]

(+)-α-HTBZ is the RRR isomer of dihydrotetrabenazine and may be referred to as (2R, 3R, 11bR) or as [+]-α-HTBZ or as (+)-α-DHTBZ or as (+)-α-HTBZ or as R,R,R-DHTBZ or as (+)-α-3-isobutyl-9,10-dimethoxy-1,3,4,6,7,11b-hexahydro-2H-pyrido[2,1-a]isoquinolin-2-ol; or as (2R, 3R,11bR)-3-isobutyl-9,10-dimethoxy-1,3,4,6,7,11b-hexahydro-2H-pyrido[2,1-a]isoquinolin-2-ol or as NBI-98782.

As used herein, "NBI-136110" means the compound which is a metabolite of valbenazine having the structure:

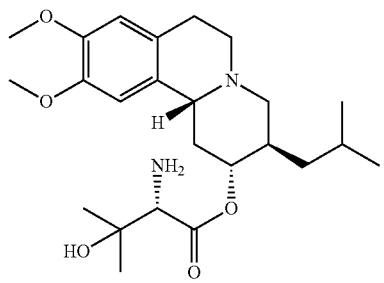 [SMILES: COc1cc2c(cc1OC)[C@H]1C[C@@H](OC(=O)[C@@H](N)C(C)(C)O)[C@H](CC(C)C)CN1CC2]

As used herein, "isotopic variant" means a compound that contains an unnatural proportion of an isotope at one or more of the atoms that constitute such a compound. In certain embodiments, an "isotopic variant" of a compound contains unnatural proportions of one or more isotopes, including, but not limited to, hydrogen (H), deuterium (2H), tritium (3H), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen (H), deuterium (2H), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), and oxygen-18 ($^{18}O$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3H$), carbon-11 ($^{11}C$), carbon-14 ($^{14}C$), nitrogen-13 ($^{13}N$), oxygen-14 ($^{14}O$), and oxygen-15 ($^{15}O$). It will be understood that, in a compound as provided herein, any hydrogen can be $^2H$, as example, or any carbon can be $^{13}C$, as example, or any nitrogen can be $^{15}N$, as example, and any oxygen can be $^{18}O$, as example, where feasible according to the judgment of one of skill in the art. In certain embodiments, an "isotopic variant" of a compound contains an unnatural proportion of deuterium.

With regard to the compounds provided herein, when a particular atomic position is designated as having deuterium or "D" or "d", it is understood that the abundance of deuterium at that position is substantially greater than the natural abundance of deuterium, which is about 0.015%. A position designated as having deuterium typically has a minimum isotopic enrichment factor of, in certain embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position. The isotopic enrichment of the compounds provided herein can be determined using conventional analytical methods known to one of ordinary skill in the art, including mass spectrometry, nuclear magnetic resonance spectroscopy, and crystallography.

As used herein, "about" means 20% of the stated value, and includes more specifically values of 10%, 5%, 2% and 1% of the stated value.

As used herein, "AUC" refers to the area under the curve, or the integral, of the plasma concentration of an active pharmaceutical ingredient or metabolite over time following a dosing event. The term "$AUC_{0-\infty}$" means the AUC from time 0 (dosing) to time infinity.

As used herein, $C_{max}$ is a pharmacokinetic parameter denoting the maximum observed blood plasma concentration following delivery of an active pharmaceutical ingredient. $C_{max}$ occurs at the time of maximum plasma concentration, $t_{max}$.

As used herein, "renal clearance" is used in its normal meaning to indicate any clearance taking place by the kidneys, e.g., by glomerular filtration, tubular excretion or degradation in the tubular cells. "Primary renal clearance" means the renal clearance is one of the major clearance pathways for a drug. Within the meaning of this application, "primary renal clearance" means that the renal clearance counts for at least 25%, at least 30%, at least 35%, at least 40%, at least 45%, at least 50%, at least 55%, at least 60%, at least 65%, at least 70%, at least 75%, at least 80%, at least 85%, or at least 90% of a drug's total clearance. In some embodiments, valbenazine does not undergo primary renal clearance.

As used herein, "substantially similar" means two values are within 0.5 to 2-fold difference. For example, after valbenazine or a pharmaceutical salt thereof is administered to a patient with normal renal function, the exposures of valbenazine and its active metabolite (+)-α-HTBZ can be measured. In some embodiments, the exposures are measured by $C_{max}$. In some embodiments, the exposures are measured by $AUC_{0-\infty}$. Similarly, the exposures of valbenazine and its active metabolite (+)-α-HTBZ can be determined in a patient with mild, moderate or severe renal impairment. Thereafter, fold changes of the exposures of valbenazine and its active metabolite (+)-α-HTBZ in a patient with mild, moderate or severe renal impairment relative to the exposures in a patient with normal renal function as references can be determined.

As used herein, "co-administer" and "co-administration" and variants thereof mean the administration of at least two drugs to a subject either subsequently, simultaneously, or consequently proximate in time to one another (e.g., within the same day, or week or period of 30 days, or sufficiently proximate that each of the at least two drugs can be simultaneously detected in the blood plasma). When co-administered, two or more active agents can be co-formulated as part of the same composition or administered as separate formulations. This also may be referred to herein as "concomitant" administration or variants thereof.

As used herein, "adjusting administration", "altering administration", "adjusting dosing", or "altering dosing" are all equivalent and mean tapering off, reducing or increasing the dose of the substance, ceasing to administer the substance to the subject, or substituting a different active agent for the substance.

As used herein, "administering to a subject" refers to the process of introducing a composition or dosage form into the subject via an art-recognized means of introduction.

As used herein, "clinically stable" means the subject is in a state of health or disease from which little if any immediate change is expected. For example, a subject is considered clinically stable if the subject has been on a consistent dosage of medication for at least one month. Clinically stable subject s may be symptomatic; however, the symptoms should be at a consistent level in terms of type and severity.

As used herein, "clinically significant" is used herein to refer to a change in a subject's clinical condition, such as a level of a side effect, that a physician treating the subject would consider to be important.

As used herein, a "dose" means the measured quantity of an active agent to be taken at one time by a subject. In certain embodiments, wherein the active agent is not valbenazine free base, the quantity is the molar equivalent to the corresponding amount of valbenazine free base. For example, often a drug is packaged in a pharmaceutically acceptable salt form, for example valbenazine ditosylate, and the dosage for strength refers to the mass of the molar equivalent of the corresponding free base, valbenazine. As an example, 73 mg of valbenazine tosylate is the molar equivalent of 40 mg of valbenazine free base.

As used herein, "dosing regimen" means the dose of an active agent taken at a first time by a subject and the interval (time or symptomatic) at which any subsequent doses of the active agent are taken by the subject such as from about 20 to about 160 mg once daily, e.g., about 20, about 40, about 60, about 80, about 100, about 120, or about 160 mg once daily. The additional doses of the active agent can be different from the dose taken at the first time.

As used herein, "effective amount" and "therapeutically effective amount" of an agent, compound, drug, composition or combination is an amount which is nontoxic, tolerable, and effective for producing some desired therapeutic effect upon administration to a subject or subject (e.g., a human subject or patient). The precise therapeutically effective amount for a subject may depend upon, e.g., the subject's size and health, the nature and extent of the condition, the therapeutics or combination of therapeutics selected for administration, and other variables known to those of skill in the art. The effective amount for a given situation is determined by routine experimentation and is within the judgment of the clinician.

As used herein, "informing" means referring to or providing published material, for example, providing an active agent with published material to a user; or presenting information orally, for example, by presentation at a seminar, conference, or other educational presentation, by conversation between a pharmaceutical sales representative and a medical care worker, or by conversation between a medical care worker and a subject; or demonstrating the intended information to a user for the purpose of comprehension.

As used herein, "labeling" means all labels or other means of written, printed, graphic, electronic, verbal, or demonstrative communication that is upon a pharmaceutical product or a dosage form or accompanying such pharmaceutical product or dosage form.

As used herein, "a "medical care worker" means a worker in the health care field who may need or utilize information regarding an active agent, including a dosage form thereof, including information on safety, efficacy, dosing, administration, or pharmacokinetics. Examples of medical care workers include physicians, pharmacists, physician's assistants, nurses, aides, caretakers (which can include family members or guardians), emergency medical workers, and veterinarians.

As used herein, the term "level of renal sufficiency" means the level of renal (kidney) function in an individual. As used herein, the levels of renal sufficiency in an individual include: no renal impairment, mild renal impairment, moderate renal impairment, severe renal impairment and end stage renal disease (ESRD). The term renal impairment includes mild renal impairment, moderate renal impairment, severe renal impairment and end stage renal disease (ESRD).

Different thresholds or cutoffs can be used to determine the level of renal sufficiency in an individual depending on the technique used and the interpretation of the health care practitioner. Several variables can be considered when determining the level of renal sufficiency in an individual including, for example, whether an individual is obese, the individual's race, the individual's gender, and the individual's age. Recommendations regarding classification of renal sufficiency are known in the art. These recommendations may change over time as newer techniques or better equations are used to more accurately determine renal function in an individual. For example, a patient with mild to moderate renal impairment may have a creatine clearance rate of 30-90 mL/min. On the other hand, a patient with severe renal impairment may have a creatine clearance rate of <30 mL/min.

As used herein, "Medication Guide" means an FDA-approved patient labeling for a pharmaceutical product conforming to the specifications set forth in 21 CFR 208 and other applicable regulations which contains information for patients on how to safely use a pharmaceutical product. A medication guide is scientifically accurate and is based on, and does not conflict with, the approved professional labeling for the pharmaceutical product under 21 CFR 201.57, but the language need not be identical to the sections of approved labeling to which it corresponds. A medication guide is typically available for a pharmaceutical product with special risk management information.

As used herein, "parkinson-like signs or symptoms" or "parkinsonism" is a general term that refers to a group of neurological conditions or disorders related to motor function similar to those seen in Parkinson's disease but that may be caused by a condition other than Parkinson's disease. The Simpson-Angus Scale (SAS) can be utilized to evaluate for parkinsonism. See, Simpson et al. (1970) Acta Psychiatry Scand Suppl 212:11-19. This scale contains 10 items: gait, arm dropping, shoulder shaking, elbow rigidity, wrist rigidity, leg pendulousness, head dropping, glabella tap, tremor, and salivation. Each item is rated between 0 and 4. A total score is obtained by adding the items and dividing by 10. Scores of up to 0.3 are considered within the normal range.

As used herein, "patient" or "individual" or "subject" means a mammal, including a human, for whom or which therapy is desired, and generally refers to the recipient of the therapy.

As used herein, "patient package insert" means information for patients on how to safely use a pharmaceutical product that is part of the FDA-approved labeling. It is an extension of the professional labeling for a pharmaceutical product that may be distributed to a patient when the product is dispensed which provides consumer-oriented information about the product in lay language, for example it may describe benefits, risks, how to recognize risks, dosage, or administration.

As used herein, "pharmaceutically acceptable" refers to a material that is not biologically or otherwise undesirable, i.e., the material may be incorporated into a pharmaceutical composition administered to a subject without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree.

As used herein, "pharmaceutically acceptable salt" means any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia, or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, by way of example only and without limitation, sodium, potassium, calcium, magnesium, ammonium, tetraalkylammonium, and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

As used herein, "crystalline" refers to a solid in which the constituent atoms, molecules, or ions are packed in a regularly ordered, repeating three-dimensional pattern. In particular, a crystalline compound or salt might be produced as one or more crystalline forms. Different crystalline forms may be distinguished by X-ray powder diffraction (XRPD) patterns.

As used herein, "substantially crystalline" refers to compounds or salts that are at least a particular weight percent crystalline. In some embodiments, the compound or salt is substantially crystalline. Examples of a crystalline form or substantially crystalline form include a single crystalline form or a mixture of different crystalline forms. Particular weight percentages include 50%, 60%, 70%, 75%, 80%, 85%, 87%, 88%, 89%, 90%, 91%, 92%, 93%, 94%, 95%, 96%, 97%, 98%, 99%, 99.5% and 99.9%. In some embodiments, substantially crystalline refers to compounds or salts that are at least 70% crystalline. In some embodiments, substantially crystalline refers to compounds or salts that are at least 80% crystalline. In some embodiments, substantially crystalline refers to compounds or salts that are at least 85% crystalline. In some embodiments, substantially crystalline refers to compounds or salts that are at least 90% crystalline. In some embodiments, substantially crystalline refers to compounds or salts that are at least 95% crystalline. In some embodiments, substantially crystalline refers to compounds or salts that are at least 98% crystalline. In some embodiments, substantially crystalline refers to compounds or salts that are at least 99% crystalline.

As used herein, a "product" or "pharmaceutical product" means a dosage form of an active agent plus published material, and optionally packaging.

As used herein, "product insert" means the professional labeling (prescribing information) for a pharmaceutical product, a patient package insert for the pharmaceutical product, or a medication guide for the pharmaceutical product.

As used herein, "professional labeling" or "prescribing information" means the official description of a pharmaceutical product approved by a regulatory agency (e.g., FDA or EMEA) regulating marketing of the pharmaceutical product, which includes a summary of the essential scientific information needed for the safe and effective use of the drug, such as, for example indication and usage; dosage and administration; who should take it; adverse events (side effects); instructions for use in special populations (pregnant women, children, geriatric, etc.); safety information for the patient, and the like.

As used herein, "published material" means a medium providing information, including printed, audio, visual, or electronic medium, for example a flyer, an advertisement, a product insert, printed labeling, an internet web site, an internet web page, an internet pop-up window, a radio or television broadcast, a compact disk, a DVD, an audio recording, or other recording or electronic medium.

As used herein, "risk" means the probability or chance of adverse reaction, injury, or other undesirable outcome arising from a medical treatment. An "acceptable risk" means a measure of the risk of harm, injury, or disease arising from a medical treatment that will be tolerated by an individual or group. Whether a risk is "acceptable" will depend upon the advantages that the individual or group perceives to be obtainable in return for taking the risk, whether they accept whatever scientific and other advice is offered about the magnitude of the risk, and numerous other factors, both political and social. An "acceptable risk" of an adverse reaction means that an individual or a group in society is willing to take or be subjected to the risk that the adverse reaction might occur since the adverse reaction is one whose probability of occurrence is small, or whose consequences are so slight, or the benefits (perceived or real) of the active agent are so great. An "unacceptable risk" of an adverse reaction means that an individual or a group in society is unwilling to take or be subjected to the risk that the adverse reaction might occur upon weighing the probability of occurrence of the adverse reaction, the consequences of the adverse reaction, and the benefits (perceived or real) of the active agent. "At risk" means in a state or condition marked by a high level of risk or susceptibility. Risk assessment consists of identifying and characterizing the nature, frequency, and severity of the risks associated with the use of a product.

As used herein, "safety" means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

As used herein, "treating" or "treatment" refers to therapeutic applications to slow or stop progression of a disorder, prophylactic application to prevent development of a disorder, and/or reversal of a disorder. Reversal of a disorder differs from a therapeutic application which slows or stops a disorder in that with a method of reversing, not only is progression of a disorder completely stopped, cellular behavior is moved to some degree, toward a normal state that would be observed in the absence of the disorder.

As used herein, "VMAT2" refers to human vesicular monoamine transporter isoform 2, an integral membrane protein that acts to transport monoamines, particularly neurotransmitters such as dopamine, norepinephrine, serotonin, and histamine, from cellular cytosol into synaptic vesicles.

As used herein, the term "VMAT2 inhibitor", "inhibit VMAT2", or "inhibition of VMAT2" refers to the ability of a compound disclosed herein to alter the function of VMAT2. A VMAT2 inhibitor may block or reduce the activity of VMAT2 by forming a reversible or irreversible covalent bond between the inhibitor and VMAT2 or through formation of a noncovalently bound complex. Such inhibition may be manifest only in particular cell types or may be contingent on a particular biological event. The term "VMAT2 inhibitor", "inhibit VMAT2", or "inhibition of VMAT2" also refers to altering the function of VMAT2 by decreasing the probability that a complex forms between a VMAT2 and a natural substrate.

In some embodiments, the VMAT2 inhibitor is chosen from (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester and pharmaceutically acceptable salts and/or isotopic variants thereof. In some embodiments, the VMAT2 inhibitor is chosen from (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester and pharmaceutically acceptable salts thereof. In some embodiments, the VMAT2 inhibitor is a tosylate salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester. In some embodiments, the VMAT2 inhibitor is a ditosylate salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester. In some embodiments, the ditosylate salt of valbenazine is substantially crystalline. In some embodiments, the crystalline ditosylate salt of valbenazine is in Form I. In some embodiments, the crystalline ditosylate salt of valbenazine has an XRPD diffraction pattern comprising X-Ray diffraction peaks at two-theta angles of 6.3, 17.9, and 19.7°±0.2°.

In some embodiments, the VMAT2 inhibitor is chosen from dihydrotetrabenazine (2-hydroxy-3-(2-methylpropyl)-1,3,4,6,7,11b-hexahydro-9,10-dimethoxy-benzo(a)quinolizine), or a pharmaceutically acceptable salt and/or isotopic variant thereof. In some embodiments, dihydrotetrabenazine is chosen from the RRR, SSS, SSRR, RSS, SSR, RRS, RSR, and SRS isomers of dihydrotetrabenazine, and mixtures thereof. In some embodiments, the VMAT2 inhibitor is the RRR isomer ((+)-α-3-isobutyl-9,10-dimethoxy-1,3,4,6,7,11b-hexahydro-2H-pyrido[2,1-a]isoquinolin-2-ol), or a pharmaceutically acceptable salt and/or isotopic variant thereof. In some embodiments, the VMAT2 inhibitor is (+)-α-3-isobutyl-9,10-dimethoxy-1,3,4,6,7,11b-hexahydro-2H-pyrido[2,1-a]isoquinolin-2-ol, or a pharmaceutically acceptable salt thereof. In some embodiments, the VMAT2 inhibitor is an isotopic variant that is (+)-α-3-isobutyl-9,10-di(methoxy-d$_3$)-1,3,4,6,7,11b-hexahydro-2H-pyrido[2,1-a]isoquinolin-2-ol or a pharmaceutically acceptable salt thereof.

As used herein "hypersensitivity" or "hypersensitivity reaction" refers to an immunological sensitization due to a drug and/or its metabolites. Generally, there are four types of hypersensitivity:

Type I, IgE mediated—immediate-type hypersensitivity, including systemic hypersensitivity (e.g., anaphylaxis and urticarial) and respiratory hypersensitivity (e.g., asthma);

Type II, IgG or IgM mediated—antibody-mediated cytotoxic reaction and Type III, IgG mediated—immune complex reaction, which often occur simultaneously and are commonly associated with systemic or organ hypersensitivity reactions. Type II and III immunopathies include anemia, leukopenia, thrombocytopenia, pneumonitis, vasculitis, lupus-like reactions or glomeronephritis; and Type IV, T lymphocyte mediated—delayed-type hypersensitivity response, which most commonly occurs as a delayed-type hypersensitivity skin reaction.

Provided is a method of administering a vesicular monoamine transporter 2 (VMAT2) inhibitor to a subject in need thereof, wherein the subject has severe renal impairment, comprising: administering the VMAT2 inhibitor to the subject in need thereof.

Also provided is a method of administering a vesicular monoamine transporter 2 (VMAT2) inhibitor to a subject in need thereof, comprising: administering the VMAT2 inhibitor to the subject in need thereof, subsequently determining that the subject has severe renal impairment, and continuing administration of the VMAT2 inhibitor.

Also provided is a method of administering a vesicular monoamine transporter 2 (VMAT2) inhibitor to a subject in need thereof, wherein the subject has mild or moderate renal impairment, comprising: administering the VMAT2 inhibitor to the subject in need thereof, subsequently determining that the subject has severe renal impairment, and continuing administration of the VMAT2 inhibitor.

Also provided is a method of treating a disease or disorder requiring a vesicular monoamine transporter 2 (VMAT2) inhibitor in a subject in need thereof, wherein the subject has severe renal impairment, comprising: administering the VMAT2 inhibitor to the subject in need thereof.

Also provided is a method of treating a neurological or psychiatric disease or disorder in a subject in need thereof, comprising: administering a vesicular monoamine transporter 2 (VMAT2) inhibitor to the subject in need thereof, wherein the subject has severe renal impairment.

Also provided herein is a method of treating a patient with tardive dyskinesia, wherein the patient has severe renal impairment, comprising:
administering to the patient a therapeutically effective amount of a vesicular monoamine transporter 2 (VMAT2) inhibitor chosen from (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester and pharmaceutically acceptable salts thereof, wherein the therapeutically effective amount is the same amount that is administered to a patient with normal renal function.

A method of treating a patient with tardive dyskinesia, comprising:

(a) orally administering to the patient a therapeutically effective amount of a vesicular monoamine transporter 2 (VMAT2) inhibitor chosen from (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester and pharmaceutically acceptable salts thereof,
(b) subsequently determining that the patient has severe renal impairment; and
(c) continuing administering the same therapeutically effective amount of the VMAT2 inhibitor.

Also provided is a method of treating a patient with tardive dyskinesia, comprising: administering a vesicular monoamine transporter 2 (VMAT2) inhibitor chosen from (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester and pharmaceutically acceptable salts thereof to the patient, wherein the patient is administered an initial dose of the VMAT2 inhibitor in an amount equivalent to about 40 mg of (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester free base once daily for one week, and an amount equivalent to about 80 mg of (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester free base once daily after one week;
subsequently determining that the patient has severe renal impairment; and continuing administering a therapeutically effective amount of the VMAT2 inhibitor to the patient. In some embodiments, the therapeutically effective amount is an amount equivalent to about 40 mg of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester free base once daily. In some embodiments, the therapeutically effective amount is an amount equivalent to about 60 mg of (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester free base once daily. In some embodiments, the therapeutically effective amount is an amount equivalent to about 80 mg of (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester free base once daily.

Also provided is a method of treating a patient with tardive dyskinesia, comprising: administering a vesicular monoamine transporter 2 (VMAT2) inhibitor chosen from (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester and pharmaceutically acceptable salts thereof to the patient, wherein the patient is administered an initial dose of the VMAT2 inhibitor in an amount equivalent to about 60 mg of (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester free base once daily for one week, and an amount equivalent to about 80 mg of (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester free base once daily after one week;
subsequently determining that the patient has severe renal impairment; and continuing administering a therapeutically effective amount of the VMAT2 inhibitor to the patient. In some embodiments, the therapeutically effective amount is an amount equivalent to about 40 mg of (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester free base once daily. In some embodiments, the therapeutically effective amount is an amount equivalent to about 60 mg of (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester free base once daily. In some embodiments, the therapeutically effective amount is an amount equivalent to about 80 mg of (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester free base once daily Also provided is the use of a VMAT2 inhibitor or a pharmaceutical composition comprising a therapeutically effective amount of a VMAT2 inhibitor for treating a patient with a neurological or psychiatric disease or disorder, wherein the patient has severe renal impairment.

Also provide is a pharmaceutical composition comprising a therapeutically effective amount of a VMAT2 inhibitor disclosed herein for use in treating a patient with a neurological or psychiatric disease or disorder, wherein the patient has severe renal impairment.

Also provided is the use of a VMAT2 inhibitor in the manufacture of a medicament for treating a patient with a neurological or psychiatric disease or disorder, wherein the patient has severe renal impairment.

In some embodiments, the subject is not on chronic dialysis.

In some embodiments, the method further comprises determining the renal sufficiency level of the subject prior to administering the VMAT2 inhibitor.

In some embodiments, the Cockcroft-Gault equation is used to determine the level of renal sufficiency of the subject. In some embodiments, the subject with severe renal impairment has a creatinine clearance rate of 15 to 29 mL/minute/1.73 m$^2$ using the Cockcroft-Gault equation. In some embodiments, the subject with mild, moderate or severe renal impairment has a creatinine clearance rate of 15 to 90 mL/minute/1.73 m$^2$ using the Cockcroft-Gault equation. In some embodiments, the subject with mild or moderate renal impairment has a creatinine clearance rate of 30 to 90 mL/minute/1.73 m$^2$ using the Cockcroft-Gault equation. The Cockcroft-Gault equation is CrCL={[(140−Age)×WT]/Scr} where CrCL is creatinine clearance (ml/min), age is in years, WT is actual body weight (kg), and Scr is serum creatinine (mg/dl); for female subjects the value is multiplied by a factor of 0.85.

In some embodiments, the subject's serum creatinine concentration is used to determine the level of renal sufficiency of the subject. In some embodiments, the subject with severe renal impairment has an approximate serum creatinine concentration of:
  less than 4.9 mg/dL for an 18-20 year old man,
  less than 3.5 mg/dL for an 18-20 year old woman,
  less than 4.5 mg/dL for a 21-30 year old man,
  less than 3.2 mg/dL for a 21-30 year old woman,
  less than 4.1 mg/dL for a 31-40 year old man,
  less than 2.9 mg/dL for a 31-40 year old woman,
  less than 2.7 mg/dL for a 41-50 year old woman,
  less than 3.3 mg/dL for a 51-60 year old man,
  less than 2.4 mg/dL for a 51-60 year old woman,
  less than 3.0 mg/dL for a man over 60 years old, or
  less than 2.0 mg/dL for a woman over 60 years old.

In some embodiments, the VMAT2 inhibitor is administered orally. In some embodiments, the VMAT2 inhibitor is administered in the form of a tablet or capsule.

In some embodiments, the VMAT2 inhibitor is administered with or without food.

In some embodiments, the amount of the VMAT2 inhibitor administered to a patient with severe renal impairment is not adjusted relative to an amount that is administered to a patient who has normal renal function or a patient who has mild or moderate renal impairment. In some embodiments, the amount of the VMAT2 inhibitor administered to a patient with severe renal impairment is equivalent to about 40 mg of valbenazine free base once daily. In some embodiments, the amount of the VMAT2 inhibitor administered to a patient severe renal impairment is equivalent to about 60 mg of valbenazine free base once daily. In some embodiments, the amount of the VMAT2 inhibitor administered to a patient with severe renal impairment is equivalent to about 80 mg of valbenazine free base once daily.

In some embodiments, a patient with severe renal impairment has substantially similar exposures of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester and its active metabolite, (+)-α-HTBZ, in the patient compared to the exposures in a patient with normal renal function who is administered the same amount of the VMAT2 inhibitor. In some embodiments, the exposure is measured by $C_{max}$. In some embodiments, the exposure is measured by $AUC_{0-\infty}$. In some embodiments, the exposure is measured by $C_{max}$ or $AUC_{0-\infty}$. In some embodiments, the exposure is measured by $C_{max}$ and $AUC_{0-\infty}$.

In some embodiments, the VMAT2 inhibitor is administered in an amount equivalent to between about 20 mg and about 160 mg of valbenazine free base. In some embodiments, the VMAT2 inhibitor is administered in an amount equivalent to between about 20 mg and about 120 mg of valbenazine free base. In some embodiments, the VMAT2 inhibitor is administered in an amount equivalent to about 20 mg of valbenazine free base. In some embodiments, the VMAT2 inhibitor is administered in an amount equivalent to about 40 mg of valbenazine free base. In some embodiments, the VMAT2 inhibitor is administered in an amount equivalent to about 60 mg of valbenazine free base. In some embodiments, the VMAT2 inhibitor is administered in an amount equivalent to about 80 mg of valbenazine free base. In some embodiments, the VMAT2 inhibitor is administered in an amount equivalent to about 120 mg of valbenazine free base.

In some embodiments, the VMAT2 inhibitor is administered in an amount equivalent to between about 20 mg and about 160 mg of valbenazine free base once daily. In some embodiments, the VMAT2 inhibitor is administered in an amount equivalent to between about 20 mg and about 120 mg of valbenazine free base once daily. In some embodiments, the VMAT2 inhibitor is administered in an amount equivalent to about 20 mg of valbenazine free base once daily. In some embodiments, the VMAT2 inhibitor is administered in an amount equivalent to about 40 mg of valbenazine free base once daily. In some embodiments, the VMAT2 inhibitor is administered in an amount equivalent to about 60 mg of valbenazine free base once daily. In some embodiments, the VMAT2 inhibitor is administered in an amount equivalent to about 80 mg of valbenazine free base once daily. In some embodiments, the VMAT2 inhibitor is administered in an amount equivalent to about 120 mg of valbenazine free base once daily.

In some embodiments, the VMAT2 inhibitor is administered for a first period of time in a first amount and then the amount is increased to a second amount. In some embodiments, the first period of time is a week. In some embodiments, the first period of time is more than one week, such as two weeks, three weeks, or four weeks. In some embodiments, the first period of time is one month, two months, three months or more. In some embodiments, the first amount is an amount equivalent to about 40 mg of valbenazine free base once daily. In some embodiments, the first amount is an amount equivalent to about 60 mg of valbenazine free base once daily. In some embodiments, the second amount is equivalent to about 60 mg of valbenazine free base once daily. In some embodiments, the second amount is equivalent to about 80 mg of valbenazine free base once daily. In some embodiment, the first amount is an amount equivalent to about 40 mg of valbenazine free base once daily and the second amount is an amount of about 60 mg of valbenazine free base once daily. In some embodiment, the first amount is an amount equivalent to about 40 mg of valbenazine free base once daily and the second amount is an amount of about 80 mg of valbenazine free base once daily. In some embodiment, the first amount is an amount equivalent to about 60 mg of valbenazine free base once daily and the second amount is an amount of about 80 mg of valbenazine free base once daily.

In some embodiments, the amount of the VMAT2 inhibitor administered to the subject is reduced relative to a subject who has normal renal impairment.

In some embodiments, the amount of the VMAT2 inhibitor is reduced by at least about 10%. In some embodiments, the amount of the VMAT2 inhibitor is reduced by at least about 20%. In some embodiments, the amount of the VMAT2 inhibitor is reduced by at least about 30%. In some embodiments, the amount of the VMAT2 inhibitor is reduced by at least about 40%. In some embodiments, the amount of the VMAT2 inhibitor is reduced by at least about 50%. In some embodiments, the amount of the VMAT2 inhibitor is reduced by at least about 60%. In some embodiments, the amount of the VMAT2 inhibitor is reduced by at least about 70%. In some embodiments, the amount of the VMAT2 inhibitor is reduced by at least about 80%. In some embodiments, the amount of the VMAT2 inhibitor is reduced by at least about 90%.

In certain embodiments, the therapeutically effective amount of the VMAT2 inhibitor is 10-90% less than the amount that would be administered to a subject who does not have severe renal impairment. In certain embodiments, the therapeutically effective amount of the VMAT2 inhibitor is 20-80% less than the amount that would be administered to a subject who does not have severe renal impairment. In certain embodiments, the therapeutically effective amount of the VMAT2 inhibitor is 30-70% less than the amount that would be administered to a subject who does not have severe renal impairment. In certain embodiments, the therapeutically effective amount of the VMAT2 inhibitor is 4-60% less than the amount that would be administered to a subject who does not have severe renal impairment. In certain embodiments, the therapeutically effective amount of the VMAT2 inhibitor is about 50% less than the amount that would be administered to a subject who does not have severe renal impairment.

For example, the amount that would be administered to a subject having severe renal impairment may be 20 mg or 40 mg per day less than a subject who does not have severe renal impairment.

For example, where the amount that would be administered to a subject who does not have severe renal impairment is 40 mg per day, an individual having severe renal impairment may receive a reduced dosage of 36, 32, 28, 24, 20, 16, 12, 8, or 4 mg per day. Likewise, where the amount that would be administered to a subject who does not have severe renal impairment is 80 mg per day, an individual having severe renal impairment may receive a reduced dosage of 72, 64, 56, 48, 40, 32, 24, 16, or 8 per day.

For example, where the dosage administered to a subject who does not have severe renal impairment is 40 mg per day, an individual having severe renal impairment may receive a reduced dosage of 4-36 mg per day, e.g., 8-32 mg per day, such as 12-28 mg per day, for example, 16-24 mg per day, or in certain embodiments, about 20 mg per day. Where the dosage administered to a subject who does not have severe renal impairment is 80 mg per day, an individual having severe renal impairment may receive a reduced dosage of 8-72 mg per day, e.g., 16-64 mg per day, such as 24-56 mg per day, for example, 32-48 mg per day, or in certain embodiments, about 24 mg per day.

For example, where the dosage administered to a subject who does not have severe renal impairment is 40 mg per day, an individual having severe renal impairment may receive a reduced dosage of 5-35 mg per day, e.g., 10-30 mg per day, such as 15-30 mg per day, for example, 15-25 mg per day, or in certain embodiments, about 20 mg per day or about 30 mg per day. Where the dosage administered to a subject who does not have severe renal impairment is 80 mg per day, an individual having severe renal impairment may receive a reduced dosage of 5-75 mg per day, e.g., 10-70 mg per day, such as 15-65 mg per day, for example, 20-60 mg per day, for example, 25-55 mg per day, for example, 30-60 mg per day, or in certain embodiments, about 40 mg per day or about 60 mg per day.

In some embodiments, the VMAT2 inhibitor is administered in an amount sufficient to achieve a maximal blood plasma concentration (Cmax) of (+)-α-DHTBZ of between about 15 ng to about 60 ng per mL plasma and a minimal blood plasma concentration (Cmin) of approximately between about at least 33%-50% of the Cmax over a 12 hour period. In some embodiments, the VMAT2 inhibitor is administered in an amount sufficient to achieve: (i) a therapeutic concentration range of about 15 ng to about 60 ng of (+)-α-DHTBZ per mL plasma; and (ii) a threshold concentration of at least 15 ng (+)-α-DHTBZ per mL plasma over a period of about 8 hours to about 24 hours.

In certain embodiments, the therapeutically effective amount is not reduced.

In some embodiments, the VMAT2 inhibitor is administered to the patient to treat a neurological or psychiatric disease or disorder. In some embodiments, the neurological or psychiatric disease or disorder is a hyperkinetic movement disorder, mood disorder, bipolar disorder, schizophrenia, schizoaffective disorder, mania in mood disorder, depression in mood disorder, treatment-refractory obsessive compulsive disorder, neurological dysfunction associated with Lesch-Nyhan syndrome, agitation associated with Alzheimer's disease, Fragile X syndrome or Fragile X-associated tremor-ataxia syndrome, autism spectrum disorder, Rett syndrome, or chorea-acanthocytosis.

In some embodiments, the neurological or psychiatric disease or disorder is a hyperkinetic movement disorder. In some embodiments, the hyperkinetic movement disorder is tardive dyskinesia. In some embodiments, the hyperkinetic movement disorder is a tic disorder. In some embodiments, the tic disorder is Tourette's Syndrome. In some embodiments, the hyperkinetic movement disorder is Huntington's disease. In some embodiments, the hyperkinetic movement disorder is choreiform movements, general dystonia, focal dystonia, and myoclonus movements. In some embodiments, the hyperkinetic movement disorder is chorea associated with Huntington's disease. In some embodiments, the hyperkinetic movement disorder is ataxia, chorea, dystonia, Huntington's disease, myoclonus, restless leg syndrome, or tremors. In some embodiments, the hyperkinetic movement disorder is a disease or disorder other than Huntington's disease. In some embodiments, the hyperkinetic movement disorder is a disease or disorder other than Huntington's disease and the VMAT2 inhibitor is deutetrabenazine or tetrabenazine.

In some embodiments, the neurological or psychiatric disease or disorder is a hyperkinetic movement disorder in patients with intellectual and developmental disability (IDD). In some embodiments, the hyperkinetic movement disorder is tardive dyskinesia in patients with intellectual and developmental disability (IDD). In some embodiments, the hyperkinetic movement disorder is a tic disorder in patients with intellectual and developmental disability (IDD). In some embodiments, the tic disorder is Tourette's Syndrome in patients with intellectual and developmental disability (IDD). In some embodiments, the hyperkinetic movement disorder is Huntington's disease in patients with intellectual and developmental disability (IDD). In some embodiments, the hyperkinetic movement disorder is choreiform movements, general dystonia, focal dystonia, and myoclonus movements in patients with intellectual and developmental disability (IDD). In some embodiments, the hyperkinetic movement disorder is chorea associated with Huntington's disease in patients with intellectual and developmental disability (IDD). In some embodiments, the hyperkinetic movement disorder is ataxia, chorea, dystonia, Huntington's disease, myoclonus, restless leg syndrome, or tremors in patients with intellectual and developmental disability (IDD). In some embodiments, the hyperkinetic movement disorder is a disease or disorder other than Huntington's disease in patients with intellectual and developmental disability (IDD). In some embodiments, the hyperkinetic movement disorder is a disease or disorder other than Huntington's disease and the VMAT2 inhibitor is deutetrabenazine or tetrabenazine in patients with intellectual and developmental disability (IDD).

In some embodiments, the intellectual and developmental disability (IDD) comprises intellectual disability and developmental disability. In some embodiments, the intellectual and developmental disability (IDD) is intellectual disability. In some embodiments, the intellectual and developmental disability (IDD) is developmental disability. In some embodiments, the intellectual and developmental disability (IDD) is characterized by the body parts or systems being affected. In a further embodiment, the body parts or systems is selected from nervous system, sensory system, metabolism, and degenerative system.

In some embodiments, the VMAT2 inhibitor is administered to the patient to treat a disease or disorder chosen from:

ataxias or spinal muscular atrophies such as spinocerebellar ataxia type 17 (SCA17)/HDL4, ataxia, spinal muscular atrophy, amyotrophic lateral sclerosis, familial amyotrophic lateral sclerosis, bulbospinal muscular atrophy congenital, dentatorubral-pallidoluysian atrophy, hereditary motor neuron disease, and hereditary spastic paraplegia;

chorea such as benign hereditary chorea, chorea, chorea associated with mitochondrial disease/causes, chorea associated with Wilson's disease, chorea gravidarum, chorea-acanthocytosis, drug-induced chorea, hemiballism, rheumatic/Sydenham's chorea, and thyrotoxic chorea/hyperthyroid chorea;

congenital malformations, deformations or abnormalities such as Angelman syndrome, congenital neurological disorder, Aicardi's syndrome, neurofibromatosis, congenital facial nerve hypoplasia, Moebius II syndrome, Cockayne's syndrome, Sjogren-Larsson syndrome, Laurence-Moon-Bardet-Biedl syndrome, Fragile X syndrome, and Prader-Willi syndrome;

dementia such as AIDS-related dementia, Alzheimer's disease, congenital neurological degeneration, Lewy body dementia, micro-infarct dementia, pre-senile dementia, senile dementia, and vascular dementia;

diseases of oral cavity, salivary glands and jaws, such as glossodynia/burning mouth syndrome and temporomandibular joint disorder;

dyskinesia such as pharyngeal dyskinesia, dyskinesia, dyskinesia (neonatal), dyskinesia (oesophageal), levodopa-induced dyskinesia, paroxysmal kinesigenic dyskinesias, paroxysmal nonkinesigneic dyskinesias, and respiratory dyskinesia;

dystonia such as blepharospasm, buccoglossal syndrome, drug-induced acute dystonia, dystonia, early onset primary dystonia, genetic torsion dystonia, hand dystonia/writer's cramp, idiopathic nonfamilial dystonia, idiopathic orofacial dystonia/Meige's disease, laryngeal dystonia, oromandibular dystonia, and spasmodic torticollis/cervical dystonia;

endocrine, nutritional and metabolic diseases such as Wilson's Disease, diabetes mellitus, obesity, syndrome X, and Lesch-Nyhan syndromes;

epilepsy such as Baltic myoclonic epilepsy, benign familial neonatal convulsions, epilepsy, epilepsy congenital, Lafora's myoclonic epilepsy, severe myoclonic epilepsy of infancy, and convulsions;

habit and impulse disorders such as binge eating disorder, kleptomania, impulse control disorders, trichotillomania, intermittent explosive disorder, pathological gambling, and pyromania;

Huntingon's disease or related disorders such as Huntington's disease, Huntington's disease-like syndromes 1-3, Huntington's chorea, and X-linked McLeod Neuroacanthocytosis syndrome;

mood or psychotic disorders such as schizophrenia, psychosis, mania, bipolar disorder, depression, and mood disorders;

other diseases or disorders such as fumbling, hypokinesia, hypokinesia (neonatal), movement disorder, rabbit syndrome, spasticity, up and down phenomenon, asthma, cancer, congenital nystagmus, familial hemiplegic migraine, fetal movement disorder, and rheumatoid arthritis;

neurotic, stress-related and somatoform disorders such as social anxiety disorder, panic disorder, generalized anxiety disorder, obsessive compulsive disorder, post-traumatic stress disorder, and psychogenic movement disorder;

other degenerative diseases of basal ganglia such as pantothethenate kinase-associated neurodegeneration, progressive supranuclear palsy, multiple system atrophy, dyslexia, basal ganglion degeneration, and neuroferritinopathy;

other extrapyramidal and movement disorders such as hemiballismus, extrapyramidal disorder, essential tremor, geniospasm, hyperexplexia, akathisia, ballismus/hemiballism, myoclonus, and restless legs syndrome/Willis-Ekbom's syndrome;

other nervous system or motor function such as sleep-related bruxism, abnormal involuntary movement disorders, alien limb syndrome, Alzheimer's disease (agitation), clumsiness, clonic hemifacial spasm, olfactory nerve agenesis, congenital cranial nerve paralysis, exercise ataxia syndrome, familial periodic paralysis, congenital hemiparesis, fine motor delay, fine motor skill dysfunction, gross motor delay, multiple sclerosis, congenital flaccid paralysis, congenital Horner's syndrome, alternating hemiplegia of childhood, motor developmental delay, cerebral palsy, athetoid cerebral palsy, posturing, pseudoparalysis, psychomotor hyperactivity, bradykinesia, synkinesis, akinesia, Riley-Day syndrome, and athetosis;

Parkinson's/parkinsonism such as parkinsonism, drug-induced parkinsonism, micrographia, and Parkinson's disease;

demoralization including demoralization and subjective incompetence pediatric-onset behavioral and emotional disorders such as attention deficit hyperactivity disorder, attention deficit disorder, hyperkinesia, hyperkinesia (neonatal), oppositional defiant disorder, provisional tic disorder, persistent (chronic) motor or vocal tic disorder, stereotypic movement disorder, stereotypy, and Tourette's syndrome;

pervasive developmental disorders such as autism spectrum disorders, Rett's syndrome, Asperger's syndrome, pervasive developmental disorder NOS, and dyslexia; and substance abuse or dependence such as addiction disorders, alcoholism, cocaine dependence, illegal drug abuse, methamphetamine abuse, methamphetamine addiction/dependence, methamphetamine use disorder, morphine abuse, morphine-analogue abuse, nicotine dependence, polysubstance abuse, and prescription drug abuse.

In some embodiments, the patient has been determined to have 22q11.2 deletion syndrome. In some embodiments, the patient is predisposed to developing a psychiatric disorder due to the patient having 22q11.2 deletion syndrome. In some embodiments, the patient has been determined to have COMT haploinsufficiency. In some embodiments, the patient is predisposed to developing a psychiatric disorder due to the patient having COMT haploinsufficiency.

In some embodiments, the patient has been determined to have Velocardiofacial syndrome (VCFS). In some embodiments, the patient with Velocardiofacial syndrome has a 3 Mb deletion. In some embodiments, the 3 Mb deletion comprises the deletion of COMT and TBX1. In some embodiments, the patient with Velocardiofacial syndrome has a 1.5 Mb deletion. In some embodiments, the 1.5 Mb deletion comprises the deletion of TBX1 and COMT.

In some embodiments, the method further comprises monitoring the subject for one or more exposure-related adverse reactions. In some embodiments, the one or more exposure-related adverse reactions is chosen from hypersensitivity reactions. In some embodiments, the one or more exposure-related adverse reactions is chosen from hypersensitivity reactions with or without dermatological reactions. In some embodiments, the one or more exposure-related adverse reactions is chosen from hypersensitivity reactions with dermatological reactions. In some embodiments, the one or more exposure-related adverse reactions is chosen from hypersensitivity reactions without dermatological reactions. In some embodiments, the one or more exposure-related adverse reactions is chosen from allergic dermatitis, angioedema, pruritus, and urticaria.

In some embodiments, hypersensitivity is Type I hypersensitivity. In some embodiments, hypersensitivity is Type IV hypersensitivity.

In some embodiments, the one or more exposure-related adverse reactions is chosen from urticaria, pruritus, allergic dermatitis, and angioedema. In some embodiments, the one or more exposure-related adverse reactions is chosen from urticaria, allergic dermatitis, and angioedema. In some embodiments, the one or more exposure-related adverse reactions is hypersensitivity reaction and rash. In some embodiments, the one or more exposure-related adverse reactions is rash. In some embodiments, the one or more exposure-related adverse reactions is chosen from rash, urticaria, and reactions consistent with angioedema.

In some embodiments, the one or more exposure-related adverse reactions is chosen from reactions consistent with angioedema. In some embodiments, the one or more exposure-related adverse reactions that are consistent with angioedema are chosen from swelling of the face, lips, and mouth, and dyspnea.

In some embodiments, the subject in need thereof who is at increased risk of one or more exposure-related adverse reactions has a history of allergies. In some embodiments, the subject has a history of allergies to one or more drugs, e.g., penicillin or paroxetine; to one or more types of food, e.g., eggs, milk, peanuts, tree nuts, fish, shellfish, wheat or soy; and/or to cats. In some embodiments, the subject has a history of hives.

In some embodiments, the method further comprises administering to the subject that is experiencing one or more exposure-related adverse reactions one or more medications chosen from steroids and antihistamines. In some embodiments, the steroid is a systemic glucocorticoid, such as prednisone. In some embodiments, the steroid is a hydrocortisone cream. In some embodiments, the antihistamine is diphenhydramine.

In some embodiments, the subject is also being administered digoxin, and the method further comprises administering to the subject a therapeutically effective amount of the VMAT2 inhibitor.

In some embodiments, the subject is also being administered digoxin, and the method further comprises administering to the subject a therapeutically effective amount of the VMAT2 inhibitor, subsequently determining that the subject is to begin treatment with digoxin, and continuing administration of the therapeutically effective amount of the VMAT2 inhibitor to the subject.

In some embodiments, the subject is also being administered digoxin, and the method further comprises administering a therapeutically effective amount of the VMAT2 inhibitor to the subject, wherein the administration produces a mean digoxin $C_{max}$ that is about 1.5 to 2.5 fold higher than the mean digoxin $C_{max}$ for a subject who is administered digoxin alone and/or a mean digoxin $AUC_{0-\infty}$ that is about 1 to about 2 fold higher than the mean digoxin $AUC_{0-\infty}$ for a subject who is administered digoxin alone.

In some embodiments, the subject is a poor metabolizer of cytochrome P450 2D6 (CYP2D6). In certain embodiments, the subject has a CYP2D6 poor metabolizer genotype. In certain embodiments, the CYP2D6 poor metabolizer genotype is chosen from the CYP2D6G1846A genotype or the CYP2D6C100T genotype. In certain embodiments, the CYP2D6 poor metabolizer genotype is one of the CYP2D6G1846A (AA) genotype or the CYP2D6G1846A (AG) genotype. In certain embodiments, the CYP2D6 poor metabolizer genotype is the CYP2D6G1846A (AA) genotype. In certain embodiments, the CYP2D6 poor metabolizer genotype is one of the CYP2D6C100T (TT) genotype or the CYP2D6C100T (CT) genotype. In certain embodiments, the CYP2D6 poor metabolizer genotype is the CYP2D6C100T (TT) genotype.

In some embodiments, administration to a subject who is a poor metabolizer of CYP2D6 results in increased exposure of (+)-α-3-isobutyl-9,10-dimethoxy-1,3,4,6,7,11b-hexahydro-2H-pyrido[2,1-a]isoquinolin-2-ol. In some embodiments, administration to a subject who is a poor metabolizer of CYP2D6 results in increased risk of one or more clinically significant parkinson-like signs or symptoms. In some embodiments, administration to a subject who is a poor metabolizer of CYP2D6 results in prolongation of the subject's QT interval. In certain embodiments, the therapeutically effective amount is less than the amount that is administered to a subject who is not a CYP2D6 poor metabolizer. In certain embodiments, the therapeutically effective amount is the same amount as that administered to a subject who is not a CYP2D6 poor metabolizer.

In some embodiments, the method further comprises monitoring the patient for one or more clinically significant parkinson-like signs or symptoms; and administering a reduced amount of the VMAT2 inhibitor to the patient, if the patient experiences one or more clinically significant parkinson-like signs or symptoms. In some embodiments, if the VMAT2 inhibitor is tetrabenazine or deutetrabenazine, the VMAT2 inhibitor is being administered to treat a disease or disorder other than Huntington's Disease.

In some embodiments, the VMAT2 inhibitor is not administered to a patient having pre-existing parkinsonism. In some embodiments, the method further comprises determining whether the patient has pre-existing parkinsonism prior to initiation of treatment with the VMAT2 inhibitor.

In some embodiments, the method further comprises administering to the patient that is experiencing one or more clinically significant parkinson-like signs or symptoms one or more medications used to treat Parkinson disease.

In some embodiments, prior to the administration, the patient is at increased risk of experiencing one or more clinically significant parkinson-like signs or symptoms. In some embodiments, the patient at increased risk of experiencing clinically significant parkinson-like signs or symptoms is a patient who is being co-administered one or more antipsychotics, antidepressants, antiepileptics, or other drugs that are known to possibly cause parkinsonism. In some embodiments, the patient at increased risk of experiencing clinically significant parkinson-like signs or symptoms is a patient having pre-existing parkinsonism.

In some embodiments, the one or more clinically significant parkinson-like signs or symptoms is chosen from difficulty moving or loss of ability to move muscles voluntarily, tremor, gait disturbances, or drooling. In some embodiments, the one or more clinically significant parkinson-like signs or symptoms is chosen from akinesia, severe tremor, gait disturbances (shuffling, festination), and drooling. In some embodiments, the one or more clinically significant parkinson-like signs or symptoms is chosen from falls, gait disturbances, tremor, drooling and hypokinesia. In some embodiments, the one or more clinically significant parkinson-like signs or symptoms is chosen from shaking, body stiffness, trouble moving or walking, or keeping balance.

In some embodiments, the one or more clinically significant parkinson-like signs or symptoms occurs within the first two weeks of administration of the VMAT2 inhibitor. In some embodiments, the one or more clinically significant parkinson-like signs or symptoms occurs within the first two weeks of increasing the amount of the VMAT2 inhibitor administered to the patient.

Also provided herein is a pharmaceutical composition comprising the VMAT2 inhibitor as an active pharmaceutical ingredient, in combination with one or more pharmaceutically acceptable carriers or excipients.

The choice of excipient, to a large extent, depends on factors, such as the particular mode of administration, the effect of the excipient on the solubility and stability of the active ingredient, and the nature of the dosage form.

The pharmaceutical compositions provided herein may be provided in unit dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules, syringes, and individually packaged tablets and capsules. Unit dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The pharmaceutical compositions provided herein may be administered alone, or in combination with one or more other compounds provided herein, one or more other active ingredients. The pharmaceutical compositions provided herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art). The pharmaceutical compositions provided herein may be administered at once, or multiple times at intervals of time. It is understood that the precise dosage and duration of treatment may vary with the age, weight, and condition of the subject being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In some embodiments, the pharmaceutical compositions has a high drug loading, as described in, e.g., PCT Publication WO 2019/060322, which is incorporated herein by reference in its entirety. In some embodiments, the pharmaceutical composition comprises a VMAT2 inhibitor, silicified microcrystalline cellulose, isomalt, hydroxypropyl methylcellulose, partially pregelatinized maize starch, and magnesium stearate. In some embodiments, the pharmaceutical composition comprises valbenazine ditosylate having a w/w % of about 40%; silicified microcrystalline cellulose having a w/w % of about 25%; isomalt having a w/w % of about 20%; hydroxypropyl methylcellulose having a w/w % of about 5%; partially pregelatinized maize starch having a w/w % of about 7.5%; and magnesium stearate having a w/w % of about 2.5%.

Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pregelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Vee gum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL®200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant. Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation. The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems.

The pharmaceutical compositions provided herein may be provided as noneffervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide. Coloring and flavoring agents can be used in all of the above dosage forms. The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action, such as antacids, proton pump inhibitors, and H2-receptor antagonists.

Dosages

In the treatment, prevention, or amelioration of one or more symptoms of disorders or other conditions, disorders or diseases associated with VMAT2 inhibition, an appropriate dosage level generally is about 0.001 to 100 mg per kg subject body weight per day (mg/kg per day), about 0.01 to about 80 mg/kg per day, about 0.1 to about 50 mg/kg per day, about 0.5 to about 25 mg/kg per day, or about 1 to about 20 mg/kg per day, which may be administered in single or multiple doses. Within this range the dosage may be 0.005 to 0.05, 0.05 to 0.5, or 0.5 to 5.0, 1 to 15, 1 to 20, or 1 to 50 mg/kg per day. In certain embodiments, the dosage level is about 0.001 to 100 mg/kg per day.

In certain embodiments, the dosage level is about from 25 to 100 mg/kg per day. In certain embodiments, the dosage level is about 0.01 to about 40 mg/kg per day. In certain embodiments, the dosage level is about 0.1 to about 80 mg/kg per day. In certain embodiments, the dosage level is about 0.1 to about 50 mg/kg per day. In certain embodiments, the dosage level is about 0.1 to about 40 mg/kg per day. In certain embodiments, the dosage level is about 0.5 to about 80 mg/kg per day. In certain embodiments, the dosage level is about 0.5 to about 40 mg/kg per day. In certain embodiments, the dosage level is about 0.5 to about 25 mg/kg per day. In certain embodiments, the dosage level is about 1 to about 80 mg/kg per day. In certain embodiments, the dosage level is about 1 to about 75 mg/kg per day. In certain embodiments, the dosage level is about 1 to about 50 mg/kg per day. In certain embodiments, the dosage level is about 1 to about 40 mg/kg per day. In certain embodiments, the dosage level is about 1 to about 25 mg/kg per day.

In certain embodiments, the dosage level is about from 5.0 to 150 mg per day, and in certain embodiments from 10 to 100 mg per day. In certain embodiments, the dosage level is about 80 mg per day. In certain embodiments, the dosage level is about 40 mg per day.

For oral administration, the pharmaceutical compositions can be provided in the form of tablets containing 1.0 to 1,000 mg of the active ingredient, particularly about 1, about 5, about 10, about 15, about 20, about 25, about 30, about 40, about 45, about 50, about 75, about 80, about 100, about 150, about 200, about 250, about 300, about 400, about 500, about 600, about 750, about 800, about 900, and about 1,000 mg of the active ingredient for the symptomatic adjustment of the dosage to the subject to be treated. In certain embodiments, the pharmaceutical compositions can be provided in the form of tablets containing about 100 mg of the active ingredient. In certain embodiments, the pharmaceutical compositions can be provided in the form of tablets containing about 80 mg of the active ingredient. In certain embodiments, the pharmaceutical compositions can be provided in the form of tablets containing about 75 mg of the active ingredient. In certain embodiments, the pharmaceutical compositions can be provided in the form of tablets containing about 50 mg of the active ingredient. In certain embodiments, the pharmaceutical compositions can be provided in the form of tablets containing about 40 mg of the active ingredient. In certain embodiments, the pharmaceutical compositions can be provided in the form of tablets containing about 25 mg of the active ingredient. The compositions may be administered on a regimen of 1 to 4 times per day, including once, twice, three times, and four times per day.

It will be understood, however, that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds provided herein may also be combined or used in combination with other agents useful in the treatment, prevention, or amelioration of one or more symptoms of the diseases or conditions for which the compounds provided herein are useful, and other conditions commonly treated with antipsychotic medication.

In certain embodiments, the compounds provided herein may also be combined or used in combination with a typical antipsychotic drug. In certain embodiments, the typical antipsychotic drug is fluphenazine, haloperidol, loxapine, molindone, perphenazine, pimozide, sulpiride, thioridazine, or trifluoperazine. In certain embodiments, the antipsychotic drug is an atypical antipsychotic drug. In certain embodiments, the atypical antipsychotic drug is aripiprazole, asenapine, clozapine, iloperidone, olanzapine, paliperidone, quetiapine, risperidone, or ziprasidone. In certain embodiments, the atypical antipsychotic drug is clozapine.

Such other agents, or drugs, may be administered, by a route and in an amount commonly used thereof, simultaneously or sequentially with the compounds provided herein. When compounds provided herein are used contemporaneously with one or more other drugs, a pharmaceutical composition containing such other drugs in addition to the compounds provided herein may be utilized, but is not required. Accordingly, the pharmaceutical compositions provided herein include those that also contain one or more other active ingredients or therapeutic agents, in addition to the compounds provided herein.

The weight ratio of the compounds provided herein to the second active ingredient may be varied, and will depend upon the effective dose of each ingredient. Generally, an effective dose of each will be used. Thus, for example, when the compounds provided herein are used in combination with the second drug, or a pharmaceutical composition containing such other drug, the weight ratio of the particulates to the second drug may range from about 1,000:1 to about 1:1,000, or about 200:1 to about 1:200.

Combinations of the particulates provided herein and other active ingredients will generally also be within the aforementioned range, but in each case, an effective dose of each active ingredient should be used.

Examples of embodiments of the present disclosure are provided in the following examples. The following examples are presented only by way of illustration and to assist one of ordinary skill in using the disclosure. The examples are not intended in any way to otherwise limit the scope of the disclosure.

EXAMPLES

Example 1

This was a Phase 1, open-label, single-dose, PK study of valbenazine to assess the safety and PK of valbenazine and its metabolites in subjects with normal renal function or severe renal impairment. A total of 16 subjects (8 with severe renal impairment and 8 with normal renal function) received a single dose of valbenazine 40 mg (free base equivalent as the ditosylate salt) under fasted conditions.

Administration of valbenazine 40 mg to subjects with severe renal impairment had no clinically meaningful effect on $C_{max}$ or $AUC_{0-\infty}$ of valbenazine, NBI-98782, or NBI-136110 compared to subjects with normal renal function (FIG. 1). Additionally, renal status had little effect on protein binding of valbenazine or NBI-98782, the active metabolite of valbenazine. There was a reduction in urine clearance of valbenazine and metabolites in subjects with severe renal impairment compared with subjects with normal renal function, but this was not associated with clinically relevant changes in systemic exposure due to the overall small fraction of administered dose excreted in urine.

Valbenazine 40 mg administered as a single dose was well tolerated in 16 subjects, including 8 subjects with normal renal function and 8 subjects with severe renal impairment. All 16 subjects completed the study and no deaths, serious or severe TEAEs, or discontinuations due to a TEAE were reported. Overall, 4 (25.0%) subjects experienced TEAEs, including 2 (25.0%) subjects from each of the renal function groups. Treatment-related TEAEs were reported in 3 subjects, including vision blurred (1 subject in the severe renal impairment group), headache (1 subject in the normal renal function group), and somnolence (1 subject in the normal renal function group and 1 subject in the severe renal impairment group).

There were no clinically significant changes in clinical laboratory tests, vital sign measurements, weight, or ECG parameters during the study and no clinically important differences were noted between groups. No subject had a QTcF interval >480 msec or an increase from baseline >60 msec.

Overall Conclusions:

Administration of valbenazine 40 mg to subjects with severe renal impairment had no clinically meaningful effect on $C_{max}$ or $AUC_{0-\infty}$ of valbenazine or metabolites compared to subjects with normal renal function.

Valbenazine was well tolerated in subjects with severe renal impairment and in subjects with normal renal function.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating a patient with tardive dyskinesia, comprising:
   administering a therapeutically effective amount of vesicular monoamine transporter 2 (VMAT2) inhibitor chosen from (S)-2-amino-3-methyl-butyric acid (2R, 3R,11bR)-3-isobutyl-9,10-dimethoxy-1,3,4,6,7,11b-hexahydro-2H-pyrido[2,1-a]isoquinolin-2-yl ester and pharmaceutically acceptable salts thereof to the patient, wherein the patient has severe renal impairment, and wherein the therapeutically effective amount is the same amount that would be administered to a patient with normal renal function.

2. The method of claim 1, wherein the therapeutically effective amount is an amount equivalent to about 40 mg of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester free base once daily.

3. The method of claim 1, wherein the therapeutically effective amount is an amount equivalent to about 60 mg of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester free base once daily.

4. The method of claim 1, wherein the therapeutically effective amount is an amount equivalent to about 80 mg of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester free base once daily.

5. The method of claim 1, wherein the VMAT2 inhibitor is administered in the form of a tablet or capsule.

6. The method of claim 1, wherein the VMAT2 inhibitor is a salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester.

7. The method of claim 6, wherein the VMAT2 inhibitor is a ditosylate salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester.

8. The method of claim 7, wherein the ditosylate salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester is in polymorphic Form I.

9. The method of claim 1, wherein the patient has a creatinine clearance of <30 mL/min.

10. The method of claim 1, wherein the exposure of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester and its active metabolite [+]-α-HTBZ in the patient with severe renal impairment is substantially similar to the exposure of (S)-2-amino-3-methyl-butyric acid (2R,3R,11bR)-3 isobutyl-9,10-dimethoxy-1,3,4,6,7,11b-hexahydro-2H-pyrido[2,1-a]isoquinolin-2-yl ester and its active metabolite [+]-α-HTBZ in the patient with normal renal function.

11. The method of claim 10, wherein the exposure is measured by $C_{max}$.

12. The method of claim 10, wherein the exposure is measured by $AUC_{0-\infty}$.

13. The method of claim 1, wherein the VMAT2 inhibitor does not undergo primary renal clearance.

14. A method of treating a patient with tardive dyskinesia, comprising:
orally administering a therapeutically effective amount of a vesicular monoamine transporter 2 (VMAT2) inhibitor chosen from (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester and pharmaceutically acceptable salts thereof to the patient;
subsequently determining that the patient has severe renal impairment; and
continuing administering the same therapeutically effective amount of the VMAT2 inhibitor to the patient.

15. The method of claim 14, wherein the VMAT2 inhibitor is administered in the form of a tablet or capsule.

16. The method of claim 14, wherein the VMAT2 inhibitor is a salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester.

17. The method of claim 16, wherein the VMAT2 inhibitor is a ditosylate salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester.

18. The method of claim 17, wherein the ditosylate salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester is in polymorphic Form I.

19. The method of claim 14, wherein the therapeutically effective amount is an amount equivalent to about 40 mg of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester free base once daily.

20. The method of claim 14, wherein the therapeutically effective amount is an amount equivalent to about 60 mg of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester free base once daily.

21. The method of claim 14, wherein the therapeutically effective amount is an amount equivalent to about 80 mg of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester free base once daily.

22. The method of claim 14, wherein the patient has a creatinine clearance of <30 mL/min.

23. The method of claim 14, wherein the exposure of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester and its active metabolite [+]-α-HTBZ in the patient with severe renal impairment is substantially similar to the exposure of (S)-2-amino-3-methyl-butyric acid (2R,3R,11bR)-3 isobutyl-9,10-dimethoxy-1,3,4,6,7,11b-hexahydro-2H-pyrido[2,1-a]isoquinolin-2-yl ester and its active metabolite [+]-α-HTBZ in the patient with normal renal function.

24. The method of claim 23, wherein the exposure is measured by $C_{max}$.

25. The method of claim 23, wherein the exposure is measured by $AUC_{0-\infty}$.

26. The method of claim 14, wherein the VMAT2 inhibitor does not undergo primary renal clearance.

27. A method of treating a patient with tardive dyskinesia, comprising:
administering a vesicular monoamine transporter 2 (VMAT2) inhibitor chosen from (S)-2-amino-3-methyl-butyric acid (2R,3R,11bR)-3-isobutyl-9,10-dimethoxy-1,3,4,6,7,11b-hexahydro-2H-pyrido[2,1-a] isoquinolin-2-yl ester and pharmaceutically acceptable salts thereof to the patient, wherein the patient is administered an initial dose of the VMAT2 inhibitor in an amount equivalent to about 40 mg of (S)-2-amino-3-methyl-butyric acid (2R,3R,11bR)-3-isobutyl-9,10-dimethoxy-1,3,4,6,7,11b-hexahydro-2H-pyrido[2,1-a] isoquinolin-2-yl ester free base once daily for one week, and an amount equivalent to about 80 mg of (S)-2-amino-3-methyl-butyric acid (2R,3R,11bR)-3- isobutyl-9,10-dimethoxy-1,3,4,6,7,11b-hexahydro-2H-pyrido[2,1-a]isoquinolin-2-yl ester free base once daily after one week;

subsequently determining that the patient has severe renal impairment; and continuing administering a therapeutically effective amount of the VMAT2 inhibitor to the patient.

28. The method of claim 27, wherein the VMAT2 inhibitor is a ditosylate salt of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester.

29. The method of claim 27, wherein the therapeutically effective amount is an amount equivalent to about 40 mg of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester free base once daily.

30. The method of claim 27, wherein the therapeutically effective amount is an amount equivalent to about 80 mg, of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester free base once daily.

\* \* \* \* \*